United States Patent [19]

Valenzuela et al.

[11] Patent Number: 5,656,473
[45] Date of Patent: Aug. 12, 1997

[54] HUMAN DMK RECEPTOR

[75] Inventors: David M. Valenzuela, Franklin Square; Eduardo A. Rojas, Tarrytown, both of N.Y.

[73] Assignee: Regeneron Pharmaceuticals, Inc., Tarrytown, N.Y.

[21] Appl. No.: 374,834

[22] Filed: Jan. 19, 1995

Related U.S. Application Data

[63] Continuation-in-part of Ser. No. 95,658, Jul. 21, 1993, abandoned.
[51] Int. Cl.[6] .......................... C12N 9/12; C07K 14/705
[52] U.S. Cl. ..................... 435/194; 530/350; 530/387.3; 435/69.1; 536/23.5
[58] Field of Search ................................. 530/350, 387.3; 435/69.1, 194; 536/23.5

[56] References Cited

PUBLICATIONS

Barinaga, Science, vol. 264, 772, 1994.
Jennings et al., PNAS, vol. 90, 2895, 1993.
Nakagawara et al., Molecular and Cellular Biology, vol. 14, 759, 1994.

*Primary Examiner*—Stephen G. Walsh
*Assistant Examiner*—Sally P. Teng
*Attorney, Agent, or Firm*—Robert J. Cobert; Gail M. Kempler

[57] ABSTRACT

The present invention provides for a gene, designated as dmk, that encodes a novel tyrosine kinase receptor expressed in high levels in denervated muscle. The invention also provides assay systems that may be used to detect and/or measure ligands that bind the dmk gene product. The present invention also provides for diagnostic and therapeutic methods based on the interaction between Dmk and agents that initiate signal transduction through binding to Dmk.

6 Claims, 10 Drawing Sheets

FIGURE 1A

```
      5        10       15        20       25       30        35       40        45       50        55       60        65      70
      *                 *                  *                  *                  *                  *                  *        *
GAATTCGGCA CGAGCAAACA GTCATTAGTG GACGACTCTA TTGTAATAAA CTGTGCTTTA AAATGTAAAC 75       80       85       90        95      100       105      110       115      120       125      130       135
      *                 *                  *                  *                  *                  *
CAGGGAGCGT TTTTTTTCCT CACATTGTCC AGAAGCAACC TTTCTTCCTG AGCCTGGATT AATC ATG
                                                                              M>

140      145       150      155       160      165       170      175       180      185       190
  *                  *                  *                  *                  *                  *
 AGA GAG CTC GTC AAC ATT CCA CTG TTA CAG ATG CTC ACC CTG GTT GCC TTC AGC GGG
  R   E   L   V   N   I   P   L   L   Q   M   L   T   L   V   A   F   S   G>

195      200      205      210       215      220       225      230       235      240       245      250
          *                 *                  *                  *                  *                  *
 ACC GAG AAA CTT CCA AAA GCC CCT GTC ATC ACC ACG CCT CTT GAA ACT GTA GAT GCC
  T   E   K   L   P   K   A   P   V   I   T   T   P   L   E   T   V   D   A>

255      260       265      270       275      280       285      290       295      300       305
      *                  *                  *                  *                  *
 TTA GTT GAA GAA GTG GCG ACT TTC ATG TGC GCC GTG GAA TCC TAC CCT CAG CCT GAA
  L   V   E   E   V   A   T   F   M   C   A   V   E   S   Y   P   Q   P   E>

310      315       320      325       330      335       340      345       350      355       360      365
  *                  *                  *                  *                  *                  *
 ATT TCT TGG ACC AGA AAT AAA ATT CTC ATC AAG CTG TTT GAC ACC CGC TAC AGC ATC
  I   S   W   T   R   N   K   I   L   I   K   L   F   D   T   R   Y   S   I>

370      375       380      385       390      395       400      405       410      415       420
      *                  *                  *                  *                  *                  *
 CGA GAG AAC GGT CAG CTC CTC ACC ATC CTG AGT GTG GAG GAC AGT GAT GAT GGC ATC
  R   E   N   G   Q   L   L   T   I   L   S   V   E   D   S   D   D   G   I>

425      430       435      440       445      450       455      460       465      470       475
  *                  *                  *                  *                  *
 TAC TGC TGC ACA GCC AAC AAT GGA GTG GGA GGA GCG GTG GAA AGT TGT GGC GCC CTG
  Y   C   C   T   A   N   N   G   V   G   G   A   V   E   S   C   G   A   L>

480      485       490      495       500      505       510      515       520      525       530      535
          *                  *                  *                  *                  *                  *
 CAA GTG AAG ATG AAG CCT AAA ATA ACT CGT CCT CCC ATC AAT GTA AAA ATA ATT GAG
  Q   V   K   M   K   P   K   I   T   R   P   P   I   N   V   K   I   I   E>

540      545       550      555       560      565       570      575       580      585       590
      *                  *                  *                  *                  *                  *
 GGA TTG AAA GCA GTC CTA CCG TGC ACT ACG ATG GGT AAC CCC AAG CCA TCC GTG TCC
  G   L   K   A   V   L   P   C   T   T   M   G   N   P   K   P   S   V   S>

595      600       605      610       615      620       625      630       635      640       645      650
          *                  *                  *                  *                  *                  *
 TGG ATT AAG GGG GAC AGT GCT CTC AGG GAA AAT TCC AGG ATT GCA GTT CTT GAA TCT
  W   I   K   G   D   S   A   L   R   E   N   S   R   I   A   V   L   E   S>

655      660       665      670       675      680       685      690       695      700       705
      *                  *                  *                  *                  *
 GGG AGT TTA AGG ATC CAT AAT GTG CAA AAG GAA GAC GCA GGA CAG TAC CGA TGT GTG
  G   S   L   R   I   H   N   V   Q   K   E   D   A   G   Q   Y   R   C   V>

710      715       720      725       730      735       740      745       750      755       760
  *                  *                  *                  *                  *
 GCA AAA AAC AGC CTG GGC ACA GCT TAC TCC AAA CTG GTG AAG CTG GAA GTG GAG GTT
  A   K   N   S   L   G   T   A   Y   S   K   L   V   K   L   E   V   E   V>
```

FIGURE 1B

```
765   770   775   780   785   790   795   800   805   810   815   820
 *                 *           *                 *                 *
TTT   GCA   AGA   ATC   CTG   CGT   GCT   CCT   GAA   TCC   CAC   AAT   GTC   ACC   TTT   GGT   TCC   TTT   GTA
 F     A     R     I     L     R     A     P     E     S     H     N     V     T     F     G     S     F     V>

825   830   835   840   845   850   855   860   865   870   875
             *                 *           *           *           *
      ACC   CTA   CGC   TGC   ACA   GCA   ATA   GGC   ATG   CCT   GTC   CCC   ACC   ATC   AGC   TGG   ATT   GAA   AAC
       T     L     R     C     T     A     I     G     M     P     V     P     T     I     S     W     I     E     N>

880   885   890   895   900   905   910   915   920   925   930   935
 *           *                       *                 *                 *
GGA   AAT   GCT   GTT   TCT   TCA   GGT   TCC   ATT   CAA   GAG   AAT   GTG   AAA   GAC   CGA   GTG   ATT   GAC
 G     N     A     V     S     S     G     S     I     Q     E     N     V     K     D     R     V     I     D>

940   945   950   955   960   965   970   975   980   985   990
             *           *           *                             *
      TCA   AGA   CTC   CAG   CTC   TTT   ATC   ACA   AAG   CCA   GGA   CTC   TAC   ACA   TGC   ATA   GCT   ACC   AAT
       S     R     L     Q     L     F     I     T     K     P     G     L     Y     T     C     I     A     T     N>

995   1000  1005  1010  1015  1020  1025  1030  1035  1040  1045
             *                 *                       *
      AAG   CAT   GGA   GAG   AAA   TTC   AGT   ACC   GCA   AAG   GCT   GCA   GCC   ACT   GTC   AGT   ATA   GCA   GAA
       K     H     G     E     K     F     S     T     A     K     A     A     A     T     V     S     I     A     E>

1050  1055  1060  1065  1070  1075  1080  1085  1090  1095  1100  1105
 *                       *                 *                 *
TGG   AGC   AAA   TCA   CAG   AAA   GAA   AGC   AAA   GGC   TAC   TGT   GCC   CAG   TAC   AGA   GGG   GAG   GTG
 W     S     K     S     Q     K     E     S     K     G     Y     C     A     Q     Y     R     G     E     V>

1110  1115  1120  1125  1130  1135  1140  1145  1150  1155  1160
                                                                   *
      TGT   GAT   GCC   GTC   CTG   GTG   AAA   GAC   TCT   CTT   GTC   TTC   TTC   AAC   ACC   TCC   TAT   CCC   GAC
       C     D     A     V     L     V     K     D     S     L     V     F     F     N     T     S     Y     P     D>

1165  1170  1175  1180  1185  1190  1195  1200  1205  1210  1215  1220
       *           *           *                       *           *     *
CCT   GAG   GAG   GCC   CAA   GAG   CTG   CTG   ATC   CAC   ACT   GCG   TGG   AAT   GAA   CTC   AAG   GCT   GTG
 P     E     E     A     Q     E     L     L     I     H     T     A     W     N     E     L     K     A     V>

1225  1230  1235  1240  1245  1250  1255  1260  1265  1270  1275
                         *           *           *                 *
      AGC   CCA   CTC   TGC   CGA   CCA   GCT   GCC   GAG   GCT   CTG   CTG   TGT   AAT   CAC   CTC   TTC   CAG   GAG
       S     P     L     C     R     P     A     A     E     A     L     L     C     N     H     L     F     Q     E>

1280  1285  1290  1295  1300  1305  1310  1315  1320  1325  1330
       *           *           *                             *
TGC   AGC   CCT   GGA   GTG   CTA   CCT   ACT   CCT   ATG   CCC   ATT   TGC   AGA   GAG   TAC   TGC   TTG   GCA
 C     S     P     G     V     L     P     T     P     M     P     I     C     R     E     Y     C     L     A>

1335  1340  1345  1350  1355  1360  1365  1370  1375  1380  1385  1390
       *           *           *           *                       *
GTA   AAG   GAG   CTC   TTC   TGT   GCA   AAG   GAA   TGG   CTG   GCA   ATG   GAA   GGG   AAG   ACC   CAC   CGC
 V     K     E     L     F     C     A     K     E     W     L     A     M     E     G     K     T     H     R>

1395  1400  1405  1410  1415  1420  1425  1430  1435  1440  1445
                         *           *                       *
      GGA   CTC   TAC   AGA   TCC   GGG   ATG   CAT   TTC   CTC   CCG   GTC   CCG   GAG   TGC   AGC   AAG   CTT   CCC
       G     L     Y     R     S     G     M     H     F     L     P     V     P     E     C     S     K     L     P>

1450  1455  1460  1465  1470  1475  1480  1485  1490  1495  1500  1505
       *           *           *                       *           *
AGC   ATG   CAC   CAG   GAC   CCC   ACA   GCC   TGC   ACA   AGA   CTG   CCG   TAT   TTA   GAT   TAT   AAA   AAA
 S     M     H     Q     D     P     T     A     C     T     R     L     P     Y     L     D     Y     K     K>
```

FIGURE 1C

```
     1510  1515  1520  1525  1530  1535  1540  1545  1550  1555  1560
     GAA AAC ATA ACA ACA TTC CCG TCC ATA ACG TCC TCC AAG CCG AGC GTG GAC ATT CCA
      E   N   I   T   T   F   P   S   I   T   S   S   K   P   S   V   D   I   P>

1565  1570  1575  1580  1585  1590  1595  1600  1605  1610  1615
     AAC CTG CCT GCC TCC ACG TCT TCC TTC GCC GTC TCG CCT GCG TAC TCC ATG ACT GTC
      N   L   P   A   S   T   S   S   F   A   V   S   P   A   Y   S   M   T   V>

1620  1625  1630  1635  1640  1645  1650  1655  1660  1665  1670  1675
ATC ATC TCC ATC ATG TCC TGC TTT GCG GTG TTT GCT CTC CTC ACC ATC ACT ACT CTC
 I   I   S   I   M   S   C   F   A   V   F   A   L   L   T   I   T   T   L>

1680  1685  1690  1695  1700  1705  1710  1715  1720  1725  1730
     TAT TGC TGC CGA AGG AGG AGA GAG TGG AAA AAT AAG AAA AGA GAG TCG GCA GCG GTG
      Y   C   C   R   R   R   R   E   W   K   N   K   K   R   E   S   A   A   V>

1735  1740  1745  1750  1755  1760  1765  1770  1775  1780  1785  1790
     ACC CTC ACC ACA TTG CCT TCC GAG CTC CTG CTG GAC AGG CTG CAT CCC AAC CCC ATG
      T   L   T   T   L   P   S   E   L   L   L   D   R   L   H   P   N   P   M>

1795  1800  1805  1810  1815  1820  1825  1830  1835  1840  1845
       TAC CAG AGG ATG CCA CTC CTT CTG AAT CCC AAG TTG CTC AGC CTG GAG TAT CCG AGG
        Y   Q   R   M   P   L   L   L   N   P   K   L   L   S   L   E   Y   P   R>

1850  1855  1860  1865  1870  1875  1880  1885  1890  1895  1900
     AAT AAC ATC GAG TAT GTC AGA GAC ATC GGA GAG GGA GCG TTT GGA AGG GTC TTT CAA
      N   N   I   E   Y   V   R   D   I   G   E   G   A   F   G   R   V   F   Q>

1905  1910  1915  1920  1925  1930  1935  1940  1945  1950  1955  1960
GCG AGG GCC CCA GGC TTG CTT CCT TAT GAA CCC TTC ACT ATG GTG GCT GTG AAG ATG
 A   R   A   P   G   L   L   P   Y   E   P   F   T   M   V   A   V   K   M>

1965  1970  1975  1980  1985  1990  1995  2000  2005  2010  2015
     CTG AAG GAG GAG GCC TCC GCA GAT ATG CAG GCA GAC TTT CAG AGG GAG GCA GCC CTC
      L   K   E   E   A   S   A   D   M   Q   A   D   F   Q   R   E   A   A   L>

2020  2025  2030  2035  2040  2045  2050  2055  2060  2065  2070  2075
ATG GCG GAG TTT GAC AAC CCC AAC ATT GTG AAG CTC TTA GGT GTG TGT GCT GTT GGG
 M   A   E   F   D   N   P   N   I   V   K   L   L   G   V   C   A   V   G>

2080  2085  2090  2095  2100  2105  2110  2115  2120  2125  2130
     AAG CCA ATG TGC CTG CTC TTT GAA TAT ATG GCC TAT GGT GAC CTC AAT GAG TTC CTC
      K   P   M   C   L   L   F   E   Y   M   A   Y   G   D   L   N   E   F   L>

2135  2140  2145  2150  2155  2160  2165  2170  2175  2180  2185
     CGA AGC ATG TCC CCT CAC ACT GTG TGC AGC CTC AGC CAC AGT GAC CTG TCC ACG AGG
      R   S   M   S   P   H   T   V   C   S   L   S   H   S   D   L   S   T   R>

2190  2195  2200  2205  2210  2215  2220  2225  2230  2235  2240  2245
GCT CGG GTG TCC AGC CCT GGT CCT CCA CCC CTG TCT TGT GCG GAA CAG CTC TGT ATT
 A   R   V   S   S   P   G   P   P   P   L   S   C   A   E   Q   L   C   I>
```

FIGURE 1D

```
     2250      2255      2260      2265      2270      2275      2280      2285      2290      2295      2300
       *                   *                   *                   *                   *                   *
     GCC AGG CAA GTG GCA GCT GGC ATG GCC TAC CTG TCG GAG CGC AAG TTT GTC CAT CGG
      A   R   Q   V   A   A   G   M   A   Y   L   S   E   R   K   F   V   H   R>

2305   2310 2315    2320      2325 2330     2335      2340 2345     2350      2355 2360
       *                   *                   *                   *                   *                   *
     GAC TTA GCT ACC AGG AAC TGC CTG GTT GGA GAG AAC ATG GTG GTG AAA ATT GCA GAC
      D   L   A   T   R   N   C   L   V   G   E   N   M   V   V   K   I   A   D>

2365   2370 2375    2380      2385 2390    2395     2400 2405     2410      2415
                   *                   *                   *                   *                   *
          TTT GGC CTC TCT AGG AAC ATC TAC TCC GCA GAC TAC TAC AAA GCT GAT GGA AAC GAT
           F   G   L   S   R   N   I   Y   S   A   D   Y   Y   K   A   D   G   N   D>

2420      2425 2430 2435     2440      2445      2450      2455      2460 2465     2470
       *                   *                   *                   *                   *                   *
     GCT ATA CCT ATC CGC TGG ATG CCA CCC GAG TCT ATC TTC TAC AAC CGC TAC ACC ACG
      A   I   P   I   R   W   M   P   P   E   S   I   F   Y   N   R   Y   T   T>

.2475 2480    2485      2490 2495     2500      2505      2510      2515      2520 2525     2530
       *                   *                   *                  .*                   *                   *
     GAG TCA GAT GTG TGG GCT TAT GGC GTG GTC CTC TGG GAG ATC TTC TCC TAT GGA CTG
      E   S   D   V   W   A   Y   G   V   V   L   W   E   I   F   S   Y   G   L>

2535 2540     2545      2550      2555      2560      2565 2570     2575      2580 2585
                   *                   *                   *                   *                   *
          CAG CCC TAC TAT GGA ATG GCC CAT GAG GAG GTC ATT TAC TAT GTG AGA GAT GGT AAC
           Q   P   Y   Y   G   M   A   H   E   E   V   I   Y   Y   V   R   D   G   N>

2590      2595 2600    2605      2610 2615    2620      2625 2630      2635      2640 2645
       *                   *                   *                   *                   *                   *
     ATC CTT GCC TGC CCT GAG AAC TGT CCC TTG GAA CTG TAC AAC CTT ATG CGC CTA TGT
      I   L   A   C   P   E   N   C   P   L   E   L   Y   N   L   M   R   L   C>

2650      2655      2660      2665      2670      2675      2680      2685      2690      2695      2700
                   *                   *                   *                   *                   *                   *
          TGG AGC AAG CTG CCT GCA GAC AGA CCC AGC TTC TGC AGT ATC CAC CGG ATC CTG CAG
           W   S   K   L   P   A   D   R   P   S   F   C   S   I   H   R   I   L   Q>

2705   2710   2715      2720      2725      2730      2735      2740   2745      2750   2755  2760
       *                   *                   *                   *                   *                   *
     CGC ATG TGC GAG AGA GCA GAG GGA ACG GTA GGC GTC TAA GGTTGACCA TGCTCAAACA
      R   M   C   E   R   A   E   G   T   V   G   V   *>

2765 2770   2775 2780    2785 2790    2795 2800    2805 2810   2815 2820    2825 2830
              *                   *                   *                   *                   *                   *
     ACACCCAGGA GGATCTTTTC AGACTGCGAG CTGGAGGGAT CCTAAAGCAG AGGGCGNATA AGNNCAGATA 2835 2840    2845 2850    2855 2860    2865
                   *                   *                   *
          GGAAGAGTTT ATCTCAGGCA GCACGTNCAG TTGGTTGTT
```

FIGURE 4A

```
            10          20          30          40          50          60
             *           *           *           *           *           *
ATG AGA GAG CTC GTC AAC ATT CCA CTG GTA CAT ATT CTT ACT CTG GTT GCC TTC AGC GGA
 M   R   E   L   V   N   I   P   L   V   H   I   L   T   L   V   A   F   S   G 70          80          90         100         110         120
             *           *           *           *           *           *
ACT GAG AAA CTT CCA AAA GCT CCT GTC ATC ACC ACT CCT CTT GAA ACA GTG GAT GCC TTA
 T   E   K   L   P   K   A   P   V   I   T   T   P   L   E   T   V   D   A   L 130         140         150         160         170         180
             *           *           *           *           *           *
GTT GAA GAA GTG GCT ACT TTC ATG TGT GCA GTG GAA TCC TAC CCC CAG CCT GAG ATT TCC
 V   E   E   V   A   T   F   M   C   A   V   E   S   Y   P   Q   P   E   I   S 190         200         210         220         230         240
             *           *           *           *           *           *
TGG ACT AGA AAT AAA ATT CTC ATT AAA CTC TTT GAC ACC CGG TAC AGC ATC CGG GAG AAT
 W   T   R   N   K   I   L   I   K   L   F   D   T   R   Y   S   I   R   E   N 250         260         270         280         290         300
             *           *           *           *           *           *
GGG CAG CTC CTC ACC ATC CTG AGT GTG GAA GAC AGT GAT GAT GGC ATT TAC TGC TGC ACG
 G   Q   L   L   T   I   L   S   V   E   D   S   D   D   G   I   Y   C   C   T 310         320         330         340         350         360
             *           *           *           *           *           *
GCC AAC AAT GGT GTG GGA GGA GCT GTG GAG AGT TGT GGA GCC CTG CAA GTG AAG ATG AAA
 A   N   N   G   V   G   G   A   V   E   S   C   G   A   L   Q   V   K   M   K 370         380         390         400         410         420
             *           *           *           *           *           *
CCT AAA ATA ACT CGC CCT CCC ATA AAT GTG AAA ATA ATA GAG GGA TTA AAA GCA GTC CTA
 P   K   I   T   R   P   P   I   N   V   K   I   I   E   G   L   K   A   V   L 430         440         450         460         470         480
             *           *           *           *           *           *
CCA TGT ACT ACA ATG GGT AAT CCC AAA CCA TCA GTG TCT TGG ATA AAG GGA GAC AGC CCT
 P   C   T   T   M   G   N   P   K   P   S   V   S   W   I   K   G   D   S   P 490         500         510         520         530         540
             *           *           *           *           *           *
CTC AGG GAA AAT TCC CGA ATT GCA GTT CTT GAA TCT GGG AGC TTG AGG ATT CAT AAC GTA
 L   R   E   N   S   R   I   A   V   L   E   S   G   S   L   R   I   H   N   V 550         560         570         580         590         600
             *           *           *           *           *           *
CAA AAG GAA GAT GCA GGA CAG TAT CGA TGT GTG GCA AAA AAC AGC CTC GGG ACA GCA TAT
 Q   K   E   D   A   G   Q   Y   R   C   V   A   K   N   S   L   G   T   A   Y 610         620         630         640         650         660
             *           *           *           *           *           *
TCC AAA GTG GTG AAG CTG GAA GTT GAG GTT TTT GCC AGG ATC CTG CGG GCT CCT GAA TCC
 S   K   V   V   K   L   E   V   E   V   F   A   R   I   L   R   A   P   E   S 670         680         690         700         710         720
             *           *           *           *           *           *
CAC AAT GTC ACC TTT GGC TCC TTT GTG ACC CTG CAC TGT ACA GCA ACA GGC ATT CCT GTC
 H   N   V   T   F   G   S   F   V   T   L   H   C   T   A   T   G   I   P   V
```

FIGURE 4B

```
          730         740         750         760         770         780
           *           *           *           *           *           *
CCC ACC ATC ACC TGG ATT GAA AAC GGA AAT GCT GTT TCT TCT GGG TCC ATT CAA GAG AGT
 P   T   I   T   W   I   E   N   G   N   A   V   S   S   G   S   I   Q   E   S 790         800         810         820         830         840
           *           *           *           *           *           *
GTG AAA GAC CGA GTG ATT GAC TCA AGA CTG CAG CTG TTT ATC ACC AAG CCA GGA CTC TAC
 V   K   D   R   V   I   D   S   R   L   Q   L   F   I   T   K   P   G   L   Y 850         860         870         880         890         900
           *           *           *           *           *           *
ACA TGC ATA GCT ACC AAT AAG CAT GGG GAG AAG TTC AGT ACT GCC AAG GCT GCA GCC ACC
 T   C   I   A   T   N   K   H   G   E   K   F   S   T   A   K   A   A   A   T 910         920         930         940         950         960
           *           *           *           *           *           *
ATC AGC ATA GCA GAA TGG AGT AAA CCA CAG AAA GAT AAC AAA GGC TAC TGC GCC CAG TAC
 I   S   I   A   E   W   S   K   P   Q   K   D   N   K   G   Y   C   A   Q   Y 970         980         990        1000        1010        1020
           *           *           *           *           *           *
AGA GGG GAG GTG TGT AAT GCA GTC CTG GCA AAA GAT GCT CTT GTT TTT CTC AAC ACC TCC
 R   G   E   V   C   N   A   V   L   A   K   D   A   L   V   F   L   N   T   S 1030        1040        1050        1060        1070        1080
           *           *           *           *           *           *
TAT GCG GAC CCT GAG GAG GCC CAA GAG CTA CTG GTC CAC ACG GCC TGG AAT GAA CTG AAA
 Y   A   D   P   E   E   A   Q   E   L   L   V   H   T   A   W   N   E   L   K 1090        1100        1110        1120        1130        1140
           *           *           *           *           *           *
GTA GTG AGC CCA GTC TGC CGG CCA GCT GCT GAG GCT TTG TTG TGT AAC CAC ATC TTC CAG
 V   V   S   P   V   C   R   P   A   A   E   A   L   L   C   N   H   I   F   Q 1150        1160        1170        1180        1190        1200
           *           *           *           *           *           *
GAG TGC AGT CCT GGA GTA GTG CCT ACT CCT ATT CCC ATT TGC AGA GAG TAC TGC TTG GCA
 E   C   S   P   G   V   V   P   T   P   I   P   I   C   R   E   Y   C   L   A 1210        1220        1230        1240        1250        1260
           *           *           *           *           *           *
GTA AAG GAG CTC TTC TGC GCA AAA GAA TGG CTG GTA ATG GAA GAG AAG ACC CAC AGA GGA
 V   K   E   L   F   C   A   K   E   W   L   V   M   E   E   K   T   H   R   G 1270        1280        1290        1300        1310        1320
           *           *           *           *           *           *
CTC TAC AGA TCC GAG ATG CAT TTG CTG TCC GTG CCA GAA TGC AGC AAG CTT CCC AGC ATG
 L   Y   R   S   E   M   H   L   L   S   V   P   E   C   S   K   L   P   S   M 1330        1340        1350        1360        1370        1380
           *           *           *           *           *           *
CAT TGG GAC CCC ACG GCC TGT GCC AGA CTG CCA CAT CTA GAT TAT AAC AAA GAA AAC CTA
 H   W   D   P   T   A   C   A   R   L   P   H   L   D   Y   N   K   E   N   L 1390        1400        1410        1420        1430        1440
           *           *           *           *           *           *
AAA ACA TTC CCA CCA ATG ACG TCC TCA AAG CCA AGT GTG GAC ATT CCA AAT CTG CCT TCC
 K   T   F   P   P   M   T   S   S   K   P   S   V   D   I   P   N   L   P   S
```

FIGURE 4C

```
      1450            1460            1470            1480            1490            1500
        *               *               *               *               *               *
TCC TCC TCT TCT TCC TTC TCT GTC TCA CCT ACA TAC TCC ATG ACT GTA ATA ATC TCC ATC
 S   S   S   S   S   F   S   V   S   P   T   Y   S   M   T   V   I   I   S   I 1510            1520            1530            1540            1550            1560
        *               *               *               *               *               *
ATG TCC AGC TTT GCA ATA TTT GTG CTT CTT ACC ATA ACT ACT CTC TAT TGC TGC CGA AGA
 M   S   S   F   A   I   F   V   L   L   T   I   T   T   L   Y   C   C   R   R 1570            1580            1590            1600            1610            1620
        *               *               *               *               *               *
AGA AAA CAA TGG AAA AAT AAG AAA AGA GAA TCA GCA GCA GTA ACC CTC ACC ACA CTG CCT
 R   K   Q   W   K   N   K   K   R   E   S   A   A   V   T   L   T   T   L   P 1630            1640            1650            1660            1670            1680
        *               *               *               *               *               *
TCT GAG CTC TTA CTA GAT AGA CTT CAT CCC AAC CCC ATG TAC CAG AGG ATG CCG CTC CTT
 S   E   L   L   L   D   R   L   H   P   N   P   M   Y   Q   R   M   P   L   L 1690            1700            1710            1720            1730            1740
        *               *               *               *               *               *
CTG AAC CCC AAA TTG CTC AGC CTG GAG TAT CCA AGG AAT AAC ATT GAA TAT GTG AGA GAC
 L   N   P   K   L   L   S   L   E   Y   P   R   N   N   I   E   Y   V   R   D 1750            1760            1770            1780            1790            1800
        *               *               *               *               *               *
ATC GGA GAG GGA GCG TTT GGA AGG GTG TTT CAA GCA AGG GCA CCA GGC TTA CTT CCC TAT
 I   G   E   G   A   F   G   R   V   F   Q   A   R   A   P   G   L   L   P   Y 1810            1820            1830            1840            1850            1860
        *               *               *               *               *               *
GAA CCT TTC ACT ATG GTG GCA GTA AAG ATG CTC AAA GAA GAA GCC TCG GCA GAT ATG CAA
 E   P   F   T   M   V   A   V   K   M   L   K   E   E   A   S   A   D   M   Q 1870            1880            1890            1900            1910            1920
        *               *               *               *               *               *
GCG GAC TTT CAG AGG GAG GCA GCC CTC ATG GCA GAA TTT GAC AAC CCT AAC ATT GTG AAG
 A   D   F   Q   R   E   A   A   L   M   A   E   F   D   N   P   N   I   V   K 1930            1940            1950            1960            1970            1980
        *               *               *               *               *               *
CTA TTA GGA GTG TGT GCT GTC GGG AAG CCA ATG TGC CTG CTC TTT GAA TAC ATG GCC TAT
 L   L   G   V   C   A   V   G   K   P   M   C   L   L   F   E   Y   M   A   Y 1990            2000            2010            2020            2030            2040
        *               *               *               *               *               *
GGT GAC CTC AAT GAG TTC CTC CGC AGC ATG TCC CCT CAC ACC GTG TGC AGC CTC AGT CAC
 G   D   L   N   E   F   L   R   S   M   S   P   H   T   V   C   S   L   S   H 2050            2060            2070            2080            2090            2100
        *               *               *               *               *               *
AGT GAC TTG TCT ATG AGG GCT CAG GTC TCC AGC CCT GGG CCC CCA CCC CTC TCC TGT GCT
 S   D   L   S   M   R   A   Q   V   S   S   P   G   P   P   P   L   S   C   A 2110            2120            2130            2140            2150            2160
        *               *               *               *               *               *
GAG CAG CTT TGC ATT GCC AGG CAG GTG GCA GCT GGC ATG GCT TAC CTC TCA GAA CGT AAG
 E   Q   L   C   I   A   R   Q   V   A   A   G   M   A   Y   L   S   E   R   K
```

FIGURE 4D

```
        2170           2180           2190           2200           2210           2220
          *              *              *              *              *              *
TTT GTT CAC CGA GAT TTA GCC ACC AGG AAC TGC CTG GTG GGC GAG AAC ATG GTG GTG AAA
 F   V   H   R   D   L   A   T   R   N   C   L   V   G   E   N   M   V   V   K 2230           2240           2250           2260           2270           2280
          *              *              *              *              *              *
ATT GCC GAC TTT GGC CTC TCC AGG AAC ATC TAC TCA GCA GAC TAC TAC AAA GCT AAT GAA
 I   A   D   F   G   L   S   R   N   I   Y   S   A   D   Y   Y   K   A   N   E 2290           2300           2310           2320           2330           2340
          *              *              *              *              *              *
AAC GAC GCT ATC CCT ATC CGT TGG ATG CCA CCA GAG TCC ATT TTT TAT AAC CGC TAC ACT
 N   D   A   I   P   I   R   W   M   P   P   E   S   I   F   Y   N   R   Y   T 2350           2360           2370           2380           2390           2400
          *              *              *              *              *              *
ACA GAG TCT GAT GTG TGG GCC TAT GGC GTG GTC CTC TGG GAG ATC TTC TCC TAT GGC CTG
 T   E   S   D   V   W   A   Y   G   V   V   L   W   E   I   F   S   Y   G   L 2410           2420           2430           2440           2450           2460
          *              *              *              *              *              *
CAG CCC TAC TAT GGG ATG GCC CAT GAG GAG GTC ATT TAC TAC GTG CGA GAT GGC AAC ATC
 Q   P   Y   Y   G   M   A   H   E   E   V   I   Y   Y   V   R   D   G   N   I 2470           2480           2490           2500           2510           2520
          *              *              *              *              *              *
CTC TCC TGC CCT GAG AAC TGC CCC GTG GAG CTG TAC AAT CTC ATG CGT CTA TGT TGG AGC
 L   S   C   P   E   N   C   P   V   E   L   Y   N   L   M   R   L   C   W   S 2530           2540           2550           2560           2570           2580
          *              *              *              *              *              *
AAG CTG CCT GCA GAC AGA CCC AGT TTC ACC AGT ATT CAC CGA ATT CTG GAA CGC ATG TGT
 K   L   P   A   D   R   P   S   F   T   S   I   H   R   I   L   E   R   M   C 2590           2600           2610
          *              *              *
GAG AGG GCA GAG GGA ACT GTG AGT GTC TAA
 E   R   A   E   G   T   V   S   V   *
```

HUMAN DMK RECEPTOR

This application is a continuation-in-part of U.S. application Ser. No. 08/095,658, filed Jul. 21, 1993, now abandoned, the contents of which are hereby incorporated by reference. Throughout this application various publications are referenced. The disclosures of these publications in their entireties are hereby incorporated by reference into this application.

INTRODUCTION

The present invention provides for novel orphan receptor molecules, their use and assay systems useful for identifying novel ligands that interact with these receptors.

BACKGROUND OF THE INVENTION

The ability of polypeptide ligands to bind cells and thereby elicit a phenotypic response such as cell growth, survival or differentiation in such cells is often mediated through transmembrane tyrosine kinases. The extracellular portion of each receptor tyrosine kinase (RTK) is generally the most distinctive portion of the molecule, as it provides the protein with its ligand-recognizing characteristic. Binding of a ligand to the extracellular domain results in signal transduction via an intracellular tyrosine kinase catalytic domain which transmits a biological signal to intracellular target proteins. The particular array of sequence motifs of this cytoplasmic, catalytic domain determines its access to potential kinase substrates (Mohammadi, et al., 1990, Mol. Cell. Biol., 11: 5068–5078; Fantl, et al., 1992, Cell, 69: 413–413).

All known growth factor RTKs appear to undergo dimerization following ligand binding (Schlessinger, J., 1988, Trend Biochem. Sci. 13: 443–447; Ullrich and Schlessinger, 1990, Cell, 61: 203–212; Schlessinger and Ullrich, 1992, Neuron 9: 383–391); molecular interactions between dimerizing cytoplasmic domains lead to activation of kinase function. In some instances, such as the growth factor platelet derived growth factor (PDGF), the ligand is a dimer that binds two receptor molecules (Hart, et al., 1988, Science, 240: 1529–1531; Heldin, 1989, J. Biol. Chem. 264: 8905–8912) while, for example, in the case of EGF, the ligand is a monomer (Weber, et al., 1984, J. Biol. Chem., 259: 14631–14636).

The tissue distribution of a particular tyrosine kinase receptor within higher organisms provides relevant data as to the biological function of the receptor. The tyrosine kinase receptors for some growth and differentiation factors, such as fibroblast growth factor (FGF) are widely expressed and therefore appear to play some general role in tissue growth and maintenance. Members of the Trk RTK family (Glass & Yancopoulos, 1993, Trends in Cell Biol, 3: 262–268) of receptors are more generally limited to cells of the nervous system, and the neurotrophins which bind these receptors promote the differentiation of diverse groups of neurons in the brain and periphery (Lindsay, R. M., 1993, in Neurotrophic Factors, S. E. Loughlin & J. H. Fallon, eds., pp. 257–284 (San Diego, Calif.: Academic Press). The localization of one such Trk family receptor, trkB, in tissue provided some insight into the potential biological role of this receptor, as well as the ligands that bind this receptor (referred to herein as cognates). Thus, for example, in adult mice, trkB was found to be preferentially expressed in brain tissue, although significant levels of trkB mRNAs were also observed in lung, muscle, and ovaries. Further, trkB transcripts were detected in mid and late gestation embryos. In situ hybridization analysis of 14 and 18 day old mouse embryos indicated that trkB transcripts were localized in the central and peripheral nervous systems, including brain, spinal cord, spinal and cranial ganglia, paravertebral trunk of the sympathetic nervous system and various innervation pathways, suggesting that the trkB gene product may be a receptor involved in neurogenesis and early neural development as well as play a role in the adult nervous system.

The cellular environment in which an RTK is expressed may influence the biological response exhibited upon binding of a ligand to the receptor. Thus, for example, when a neuronal cell expressing a Trk receptor is exposed to a neurotrophin which binds that receptor, neuronal survival and differentiation results. When the same receptor is expressed by a fibroblast, exposure to the neurotrophin results in proliferation of the fibroblast (Glass, et al., 1991, Cell 66: 405–413). Thus, it appears that the extracellular domain provides the determining factor as to the ligand specificity, and once signal transduction is initiated the cellular environment will determine the phenotypic outcome of that signal transduction.

A number of RTK families have been identified based on sequence homologies in their intracellular domain. For example, two members of the TIE (tyrosine kinase with immunoglobulin and EGF homology domains) family, known as TIE-1 and TIE-2, have 79% sequence homology in their intracellular region (Maisonpierre, et al., 1993, Oncogene 8: 1631–1637). Although these receptors share similar motifs in their extracellular domain, only 32% of the sequences are identical. This indicates potentially divergent biological roles which are reflected in the fact that while both genes are widely expressed in endothelial cells of embryonic and postnatal tissue, significant levels of tie-2 transcripts are also present in other embryonic cell populations that include lens epithelium, heart epicardium and regions of mesenchyme.

The receptor and signal transduction pathways utilized by NGF involve the product of the trk proto-oncogene. (Kaplan et al., 1991, Nature 350: 156–160; Klein et al., 1991, Cell 65: 189–197). Klein et al. (1989, EMBO J. 8: 3701–3709) reported the isolation of trkB, which encodes a second member of the tyrosine protein kinase family of receptors found to be highly related to the human trk proto-oncogene. TrkB binds and mediates the functional responses to BDNF, NT-4, and to a lesser extent, NT-3 (Squinto, et al., 1991, Cell 65: 885–903; Ip, et al., 1992, Proc. Natl. Acad. Sci. U.S.A. 89: 3060–3064; Klein, et al., 1992, Neuron, 8: 947–956). At the amino acid level, the products of trk and trkB were found to share 57 percent homology in their extracellular regions, including 9 of the 11 cysteines present in trk. This homology was found to increase to 88 percent within their respective tyrosine kinase catalytic domains. The Trk gene family has now been expanded to include the trkC locus, with NT-3 having been identified as the preferred ligand for trkC (Lamballe, et al., 1991, Cell 66: 967–979).

Two novel human genes, ror1 and ror2, encode proteins which have in their cytoplasmic portion a region homologous to proteins differ considerably from the Trk family in their extracellular portion (Masiakowski and Carroll, 1992, J. Biol. Chem. 267: 26181–26190).

Another receptor having a kinase domain that is related to the Trk family has been identified in the electric ray Torpedo californica and may play a role in motor neuron induced synapses on muscle fibers. Jennings, et al. Proc. Natl. Acad. Sci. USA 90: 2895–2899 (1993). This kinase was isolated from the electric organ, tissue which is homologous to muscle. Like the rors, the tyrosine kinase domain of this protein is related to the Trk family, while the extracellular domain is somewhat divergent from the Trks. The protein was found to be expressed at high levels in Torpedo skeletal muscle, and at much lower levels in adult Torpedo brain, spinal cord, heart, liver and testis.

Because RTKs appear to mediate a number of important functions during development, the identification and isolation of novel RTKs may be used as a means of identifying new ligands that may play a crucial role in development. Often such novel RTKs are identified and isolated by searching for additional members of known families of tyrosine kinase receptors using, for example, PCR-based screens involving known regions of homology among Trk family members. (See, for example, Maisonpierre, et al., 1993, Oncogene 8: 1631–1637). Isolation of such so called "orphan" tyrosine kinase receptors, for which no ligand is known, and subsequent determination of the tissues in which such receptors are expressed, provides insight into the regulation of the growth, proliferation and regeneration of cells in target tissues. Further, such receptors may be used to isolate their cognate ligand, which may then be used to regulate the survival, growth and regeneration of cells expressing the receptor.

SUMMARY OF THE INVENTION

The present invention provides for a novel tyrosine kinase, termed "Dmk" for "denervated muscle kinase", which is expressed in normal and denervated muscle, as well as other tissues including heart, spleen and retina. The protein appears to be related to the Trk family of tyrosine kinases.

The present invention further provides for an isolated nucleic acid molecule encoding Dmk.

The present invention also provides for a protein or peptide that comprises the extracellular domain of Dmk and the nucleic acid which encodes such extracellular domain.

The invention further provides for vectors comprising an isolated nucleic acid molecule encoding Dmk or its extracellular domain, which can be used to express Dmk in bacteria, yeast and mammalian cells.

The present invention further provides for use of the Dmk receptor or its extracellular or intracellular domain in screening for drugs that interact with Dmk. Novel agents that bind to the receptor(s) described herein may mediate survival and differentiation in cells naturally expressing the receptor, but also may confer survival and proliferation when used to treat cells engineered to express the receptor. In particular embodiments, the extracellular domain (soluble receptor) of Dmk is utilized in screens for cognate ligands.

The invention also provides for a nucleic acid probe capable of hybridizing with a sequence included within the nucleic acid sequence encoding human Dmk useful for the detection of Dmk expressing tissue in humans and animals.

The invention further provides for antibodies directed to Dmk.

The present invention also has diagnostic and therapeutic utilities. In particular embodiments of the invention, methods of detecting aberrancies in the function or expression of the receptor described herein may be used in the diagnosis of muscular or other disorders. In other embodiments, manipulation of the receptor or agonists which bind this receptor may be used in the treatment of neurological diseases, diseases of muscle or neuromuscular unit disorders, including Alzheimer's disease, Parkinson's disease, amyotrophic lateral sclerosis (Lou Gehrig's disease) and idiopathic torsion dystonia. In further embodiments, the extracellular domain of the receptor is utilized as a blocking agent which blocks the binding of receptor to target cells.

In a further embodiment of the invention, patients that suffer from an excess of Dmk may be treated by administering an effective amount of anti-sense RNA or anti-sense oligodeoxyribonucleotides corresponding to the dmk gene coding region, thereby decreasing expression of Dmk.

BRIEF DESCRIPTION OF THE FIGURES

FIG. 1—Nucleic acid and deduced amino acid (single letter code) sequences of dmk SEQ ID NOS: 1 and 2. The nucleotide sequence encoding mature Dmk begins around nucleotide 192.

FIG. 4—Nucleotide and deduced amino acid (single letter code) sequences of human Dmk receptor (SEQ ID NOS: 16 and 17).

DETAILED DESCRIPTION OF THE INVENTION

Figure 2:
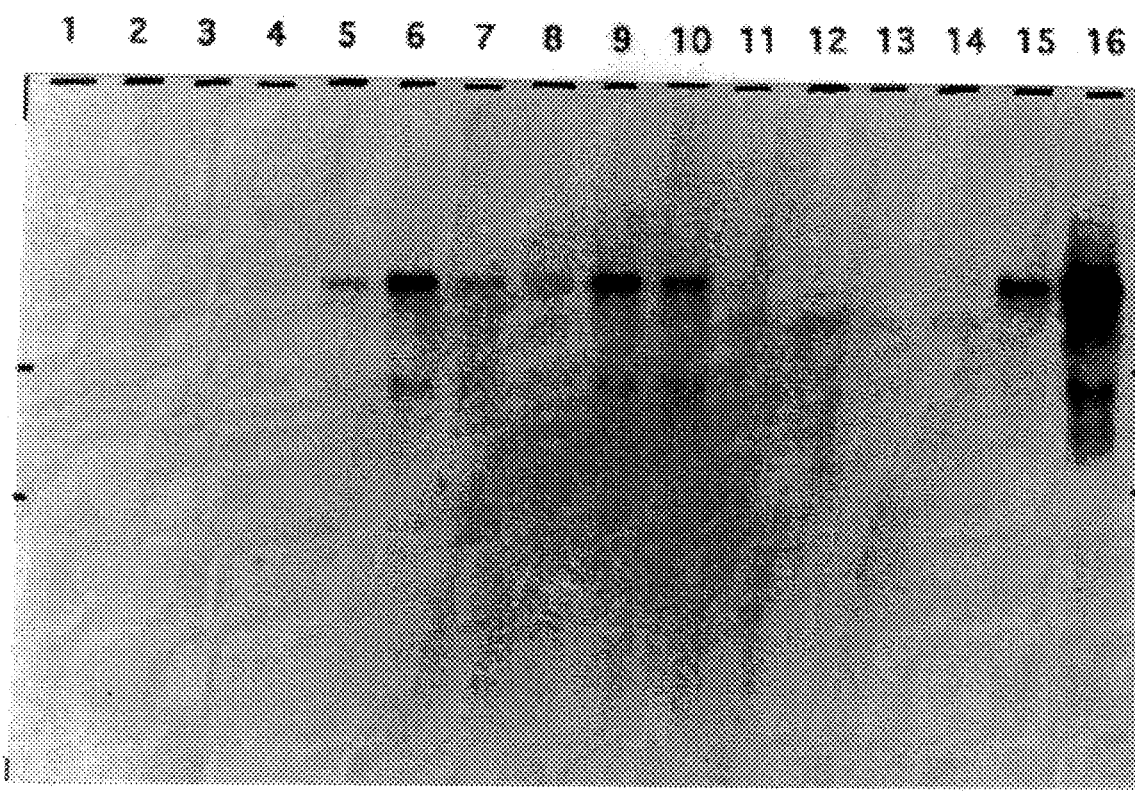
FIG. 2—Northern blot showing distribution of dmk in the rat during early development. Lane 1: Total embryo E9; Lane 2: Total embryo E11; Lane 3: Placenta E11; Lane 4: Embryo head E12; Lane 5: Embryo body E12; Lane 6: Embryo spinal cord E12; Lane 7: Placenta E12; Lane 8: Embryo head E13; Lane 9: Embryo body E13; Lane 10: Embryo brain E17; Lane 11: Embryo brain P1; Lane 12: Embryo brain P10; Lane 13: Embryo brain P19; Lane 14: Adult brain; Lane 15: Adult muscle; Lane 16: Adult denervated muscle; where day of sperm positivity is designated as day E1, and day of birth is designated as day P1.

The present invention provides for a novel tyrosine kinase molecule that is related to the trk family of tyrosine kinases. The sequence of the protein is set forth in FIG. 1 as SEQ. ID NO: 1. The coding region of the mature protein is believed to begin on or around the serine-glycine-threonine on or around position 20 of the coded region.

The novel tyrosine kinase described herein has been found to be induced in denervated skeletal muscle. Accordingly, it has been tentatively designated as Dmk (denervated muscle kinase). In addition to being found in muscle, both normal and denervated, and, in particular, in the heart, Dmk has also been found to have a substantial presence in, but does not appear to be limited to, the spleen, ovary and retina. It appears to be present during early development, but is also found in adult tissue.

Dmk may be related to the Torpedo RTK identified by Jennings, et al. supra. It differs, however, in that it appears to be induced in denervated muscle, whereas no such induction has been reported with regard to the Torpedo RTK. Furthermore, the Torpedo RTK has an extracellular kringle domain, whereas Dmk does not. However, these kinases may be members of the same or related families.

The gene encoding rat Dmk has been cloned and the DNA sequence determined (FIG. 1; SEQ ID NO: 2). The extracellular domain of the mature protein is believed to be encoded by the nucleic acid sequence beginning on or around position 192 and ending on or around position 1610. The transmembrane portion of the protein is believed to be encoded by the nucleic acid sequence beginning on or around position 1611 and ending on or around position 1697. The intracellular domain is believed to be encoded by the nucleic acid sequence beginning on or around position 1698 and ending on or around position 2738. A cDNA clone encoding Dmk was deposited with the American Type Culture Collection on Jul. 13, 1993 and accorded an accession number of ATCC No. 75498.

The present invention also provides for a protein or peptide that comprises the extracellular domain of Dmk as well as the sequence of nucleic acids which encode this extracellular domain. The extracellular domain of the protein is believed to be comprised of the amino acids at or around positions 20 through 492 of the coding region set forth as SEQ ID NO: 1.

Dmk in rat may be used to identify the comparable protein in human using the materials and methods described herein to search in human libraries, preferably derived from muscle. In addition, the similarity between Dmk and the Torpedo RTK suggests the utilization of regions of sequence homologies within these genes to develop primers useful for searching for additional, related RTKs.

Accordingly, the invention provides for nucleic acids, or oligonucleotides greater than about 10 bases in length, that hybridize to the Dmk-encoding DNA described herein and that remain stably bound to it under stringent conditions. Stringent conditions as used herein are those which (1) employ low ionic strength and high temperature for washing, for example, 0.15M NaCl/0.015M sodium citrate/ 0.1% NaDodSO$_4$ at 50° C., or (2) use during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.

The present invention further provides for an isolated and purified nucleic acid molecule comprising a nucleic acid sequence encoding human denervated muscle kinase (Dmk) receptor, wherein the nucleic acid sequence is selected from the group consisting of:

(a) the nucleic acid sequence comprising the coding region of the human Dmk receptor as set forth in FIG. 4 (SEQ ID NO: 17);

(b) a nucleic acid sequence that hybridizes under stringent conditions to the nucleic acid sequence of (a) and which encodes a human Dmk receptor; and (c) a nucleic acid sequence that is degenerate as a result of the genetic code to a nucleic acid sequence of (a) or (b), and which encodes a human Dmk receptor.

The invention further provides for isolated and purified human Dmk receptor encoded by the coding region of the human Dmk receptor as set forth above. The invention also provides for a vector which comprises the isolated nucleic acid molecule described. In one embodiment, the vector is an expression vector wherein the DNA molecule is operatively linked to an expression control sequence. In a further embodiment, the expression vector comprises an immediate early gene promoter. In a still further embodiment, the expression vector of the invention comprises the fos promoter or the jun promoter as the early gene promoter.

The invention further contemplates a host-vector system for the production of a polypeptide having the biological activity of a human Dmk receptor which comprises the vector described above in a suitable host cell. By way of nonlimiting example, a suitable host cell may be a PC12 cell or an NIH3T3 cell. The invention further provides for a method of producing a polypeptide having the biological activity of human Dmk receptor which comprises growing cells of the above-described host-vector system under conditions permitting production of the polypeptide and recovering the polypeptide so produced.

In addition, the invention provides for a therapeutic composition comprising the above-described Dmk receptor in a pharmaceutically acceptable vehicle.

The invention also provides for an antibody which specifically binds the above-described Dmk receptor. The antibody of the invention may be a polyclonal or monoclonal antibody.

The invention further provides for a receptorbody comprising the extracellular portion of the above-described Dmk receptor, fused to an immunoglobulin constant region. In a preferred embodiment, the constant region is the human immunoglobulin gamma-1 constant region.

The invention also provides for a fibroblast cell line that is growth factor dependent in serum-free medium and that comprises a nucleic acid molecule encoding the human Dmk receptor as described above.

When using nucleotide sequences coding for part or all of Dmk in accordance with this invention to isolate new family members or Dmk from other species, the length of the sequence should be at least sufficient to be capable of hybridizing with endogenous mRNA from the vertebrate's own dmk. Typically, sufficient sequence size will be about 15 consecutive bases (DNA or RNA).

Strategies for identifying novel RTKs using degenerate oligodeoxyribonucleotide primers corresponding to protein regions surrounding amino acids conserved in tyrosine kinases have been previously described (Wilks, et al., 1989, Proc. Natl. Acad. Sci. U.S.A., 86: 1603–1607, Partanen, J. et al., 1990, Proc. Natl. Acad. Sci. U.S.A. 87: 8913–8917; Lai and Lemke, 1991, Neuron 6: 691–704; Masiakowski and Carroll, 1992, J. Biol. Chem. 267: 26181–26190). The discovery by applicants of the relationship between Dmk and the Torpedo RTK has led to the identification of heretofore unknown homology regions which may be used in screening strategies.

The following primer, based on the amino acid homology domain Asp-Val-Trp-Ala-Tyr-Gly (SEQ ID NO: 3) between Dmk and the Torpedo RTK, may be used in combination with additional primers that correspond to known homology regions characteristic of RTKs, to isolate related tyrosine kinases, e.g. other family members [all codes used herein representing amino acids and nucleotides are as set forth in 37 C.F.R. §1.822(b)]:

5'-GAATTCGAGCTCCCRWANGCCCANACRTC-3' (SEQ ID NO: 4)

The additional primers that correspond to known homology regions characteristic of RTKs include the following:
5'
1) Asp-Leu-Ala-Thr-Arg-Asn (SEQ ID NO: 5)
   5'-TCTTGACTCGAGAYYTNGCNACNMGNAA-3' (SEQ ID NO: 6)
2) Asp-Leu-Ala-Ala-Arg-Asn (SEQ ID NO: 7)
   5'-TCTTGACTCGAGAYYTNGCNGCNMGNAA-3' (SEQ ID NO: 8)
3'
1) Asp-Val-Trp-Ser-Leu-Gly (SEQ ID NO: 9)

3'-CTRCANACCWSNATRCCCTCGAGCTTAAG-5' (SEQ ID NO: 10)

2) Asp-Val-Trp-Ser-Phe-Gly (SEQ ID NO: 11)
3'-CTRCANACCWSNAARCCCTCGAGCTTAAG-5' (SEQ ID NO: 12)

3) Asp-Val-Trp-Ser-Tyr-Gly (SEQ ID NO: 13)
3'-CTRCANACCWSNRANCCCTCGAGCTTAAG-5' (SEQ ID NO:14)

Alternatively, regions of homology shared by Dmk and members of related families, such as the Trk family, may be used in strategies designed to isolate novel RTKs.

The present invention further provides for substantially purified protein molecules comprising the amino acid sequence substantially as set forth in FIG. 1 for Dmk (SEQ ID NO: 1) or functionally equivalent molecules. Functionally equivalent molecules include those in which amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which are differentially modified during or after translation, e.g., by glycosylation, proteolytic cleavage, linkage to an antibody molecule or other cellular ligand, etc.

The invention further contemplates the isolation of proteins that have substantial similarity to the Dmk protein described herein. Substantial similarity, as used herein, refers to proteins that are Dmk from different species or family members within a species that are identical in at least 40% of positions. Substantial similarity at the protein level includes an ability of a subject protein to compete with Dmk for binding to monoclonal antibodies raised against Dmk epitopes. The Dmk protein described herein is useful in 1) screening strategies, 2) purification strategies and 3) diagnostic uses. With respect to screening strategies, expression cloning strategies based on cell survival and proliferation assays provide a method of screening for cognate ligands (Glass, et al. (1991) Cell 66: 405–413). Since ligands that bind Dmk may be membrane bound, other strategies for identification of such receptors may be more well suited (Armitage, et al. 1992, Nature 357: 80–82; Smith, et al. 1993, Cell 73: 1349–1360). In preferred embodiments, the extracellular domain of Dmk is fused to a marker to create a chimeric protein which enables identification and purification of the extracellular domain when bound to a cognate.

If, for example, the cognate ligand is membrane bound, as described in Smith, et al. supra, the extracellular portion of Dmk may be fused to truncated immunoglobulin heavy chains (Fc). The fusion product may then be used to identify cells expressing surface ligand that binds the receptor by, for example, flow cytometry. Alternatively, other tags, such as myc used to tag the extracellular domain of Dmk, may also be useful for the screening and purification of Dmk-binding ligands (Davis, et al. 1991, Science 253: 59–63; Squinto, et al., 1990, Neuron 5: 757–766).

In other embodiments, the extracellular portion of RTKs that bind known ligands are replaced with the extracellular portion of Dmk. Measurable effects, such as changes in phenotype or induction of early response genes, normally associated with binding of the known ligand to the receptor, can be used to screen for cognate ligands that induce comparable effects.

For example, a cell line bearing the introduced Dmk receptor or a chimeric protein comprising the extracellular domain of Dmk fused to the transmembrane domain and intracellular domain of another RTK (Dmk-chimeric receptor), as well as the parental cell line without the receptor can be exposed to any potential source of an agent that might work through the receptor. Any specific effects (e.g. on cell survival or proliferation) on the cell line bearing the receptor or chimera can be used to identify and eventually purify agents acting on that receptor. Once a particular receptor/ligand system is defined, a variety of additional specific assay systems can be utilized, for example, to search for additional agonists or antagonists of Dmk.

According to the invention, Dmk or a Dmk-RTK chimeric receptor, when introduced into cells that do not normally express this receptor, can be used to identify ligands that bind the receptor based on the distinguishable response of the cell. The present invention contemplates that the type of response elicited depends on the cell utilized, and not the specific receptor introduced into the cell. Thus, for example, expression of the Dmk receptor in PC12 pheochromocytoma cells may result in the differentiation of the PC12 cells upon exposure to a ligand that binds the receptor, whereas the same receptor in fibroblasts may mediate both survival and proliferation in response to a Dmk binding ligand. Appropriate cell lines can be chosen to yield a response of the greatest utility for the assay, as well as discovery of agents that can act on tyrosine kinase receptors. "Agents" refers to any molecule(s), including but not limited to peptide and non-peptide molecules, that will act in systems to be described in a receptor dependent manner. One of the more useful systems to be exploited involves the introduction of the desired receptor into a growth factor dependent fibroblast cell line. Such a receptor which does not normally mediate proliferative responses may, following introduction into fibroblasts, nonetheless be assayed by a variety of well established methods used to quantitate effects of fibroblast growth factors (e.g. thymidine incorporation or other types of proliferation assays; see van Zoelen, 1990, "The Use of Biological Assays For Detection Of Polypeptide Growth Factors" in Progress in Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor. Only specific effects on the cell line with the receptor would be judged as being mediated through the introduced receptor.

A cell that expresses an orphan receptor described herein may either naturally express the receptor or be genetically engineered to do so. For example, nucleic acid sequences obtained as described in section 6 or 8, infra, may be introduced into a cell by transfection, transduction, microinjection, electroporation, via a transgenic animal, etc., using any method known in the art.

The specific binding of test agent to the orphan receptor may be measured in a number of ways. For example, the binding of test agent to cells may be detected or measured, by detecting or measuring (i) test agent bound to the surface of intact cells; (ii) test agent cross-linked to receptor protein in cell lysates; or (iii) test agent bound to receptor in vitro. The specific interaction between test agent and the receptor may be evaluated by using reagents that demonstrate the unique properties of that interaction.

Alternatively, the specific binding of test agent to the receptor may be measured by evaluating the secondary biological effects of receptor/ligand binding, including, but not limited to, the induction of neurite sprouting, immediate early gene expression or phosphorylation of the receptor. For example, the ability of the test agent to induce neurite sprouting can be tested in cells that lack the receptor and in comparable cells that express, for example, a chimeric receptor comprising the Dmk extracellular domain and the intracellular domain of a member of the Trk family; neurite sprouting in receptor-expressing cells but not in comparable cells that lack the receptor would be indicative of a specific test agent/receptor interaction. A similar analysis could be performed by detecting immediate early gene (e.g. fos and jun) induction in receptor-minus and receptor-plus cells, or by detecting phosphorylation of the receptor protein using standard phosphorylation assays known in the art.

Similarly, the present invention provides for a method of identifying an agent that has signal transducing activity comprising (i) exposing a cell that expresses a tyrosine kinase receptor as described herein to a test agent and (ii) detecting the specific binding of the test agent to the receptor, in which specific binding to the receptor positively correlates with signal transducing activity. Specific binding may be detected by either assaying for direct binding or the secondary biological effects of binding, as discussed supra. Such a method may be particularly useful in identifying new neurotrophic factors or factors having other pharmaceutical activity such as cardioprotective activity, or may be useful in screening a large array of peptide and non-peptide agents (e.g., peptidomimetics) for such activities.

In a preferred, specific, nonlimiting embodiment of the invention, a large grid of culture wells may be prepared that contain, in alternate rows, PC12 (or fibroblasts, see infra) cells that are either receptor-minus or engineered to be receptor-plus. A variety of test agents may then be added such that each column of the grid, or a portion thereof, contains a different test agent. Each well could then be scored for the presence or absence of neurite sprouting. An extremely large number of test agents could be screened for signal transducing activity in this manner.

The present invention also provides for assay systems that may be used according to the methods described supra. Such assay systems may comprise in vitro preparations of receptor, e.g. affixed to a solid support, or may preferably comprise cells that express receptor proteins described herein.

The present invention further provides for host cells and microorganisms and vectors that carry the recombinant nucleic acid molecules described above including, but not limited to, Dmk.

Cells that express receptor protein may be genetically engineered to produce receptor as described supra, by transfection, transduction, electroporation, or microinjection of nucleic acid encoding Dmk in a suitable expression vector. In one embodiment, the host cell carrying the recombinant nucleic acid is an animal cell, such as COS. In another embodiment, the host cell is a bacterium, preferably *Escherichia coli*.

Any of the methods known to one skilled in the art for the insertion of DNA fragments into a vector may be used to construct expression vectors encoding receptor. These methods may include in vitro recombinant DNA and synthetic techniques and in vivo recombinations (genetic recombination). Expression of nucleic acid sequence encoding the receptor protein or peptide fragment may be regulated by a second nucleic acid sequence so that the receptor protein or peptide is expressed in a host transformed with the recombinant DNA molecule. For example, expression of receptor may be controlled by any promoter/enhancer element known in the art. Promoters which can be used to control receptor expression include, but are not limited to the long terminal repeat as described in Squinto et al., (1991, Cell 65: 1–20); the SV40 early promoter region (Bernoist and Chambon, 1981, Nature 290: 304–310), the CMV promoter, the M-MuLV 5' terminal repeat the promoter contained in the 3' long terminal repeat of Rous sarcoma virus (Yamamoto, et al., 1980, Cell 22: 787–797), the herpes thymidine kinase promoter (Wagner et al., 1981, Proc. Natl. Acad. Sci. U.S.A. 78: 144–1445), the regulatory sequences of the metallothioein gene (Brinster et al., 1982, Nature 296: 39–42); prokaryotic expression vectors such as the β-lactamase promoter (Villa-Kamaroff, et al., 1978, Proc. Natl. Acad. Sci. U.S.A. 75: 3727–3731), or the tac promoter (DeBoer, et al., 1983, Proc. Natl. Acad. Sci. U.S.A. 80: 21–25). See also "Useful proteins from recombinant bacteria" in Scientific American, 1980, 242: 74–94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38: 639–646; Ornitz et al., 1986, Cold Spring Harbor Symp. Quant. Biol. 50: 399–409;MacDonald, 1987, Hepatology 7: 425–515); insulin gene control region which is active in pancreatic beta cells (Hanahan, 1985, Nature 315: 115–122), immunoglobulin gene control region which is active in lymphoid cells (Girosschedl et al., 1984, Cell 38: 647–658; Adames et al., 1985, Nature 318: 533–538; Alexander et al., 1987, Mol. Cell. Biol. 7: 1436–1444), mouse mammary tumor virus control region which is active in testicular, breast, lymphold and mast cells (Leder et al., 1986, Cell 45: 485–495), albumin gene control region which is active in liver (Pinkert et al., 1987, Genes and Devel. 1: 268–276), alpha-fetoprotein gene control region which is active in liver (Krumlauf et al., 1985, Mol. Cell. Biol. 5: 1639–1648; Hammer et al., 1987, Science 235: 53–58); alpha 1-antitrypsin gene control region which is active in the liver (Kelsey et al, 1987, Genes and Devel. 1: 161–171), beta-globin gene control region which is active in myeloid cells (Mogram et al., 1985, Nature 315: 338–340; Kollias et al., 1986, Cell 46: 89–94); myelin basic protein gene control region which is active in oligodendrocyte cells in the brain (Readhead et al., 1987, Cell 48: 703–712); myosin light chain-2 gene control region which is active in skeletal muscle (Sani, 1985, Nature 314: 283–286), and gonadotropic releasing hormone gene control region which is active in the hypothalamus (Mason et al., 1986, Science 234: 1372–1378).

Expression vectors containing receptor-encoding gene inserts can be identified by three general approaches: (a) DNA—DNA hybridization, (b) presence or absence of "marker" gene functions, and (c) expression of inserted sequences. In the first approach, the presence of a foreign gene inserted in an expression vector can be detected by DNA—DNA hybridization using probes comprising sequences that are homologous to an inserted gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if the receptor-encoding gene is inserted within the marker gene sequence of the vector, recombinants containing the gene insert can be identified by the absence of the marker gene function. In the third approach, recombinant expression vectors can be identified by assaying the foreign gene product expressed by the recombinant vector. Such assays can be based, for example, on the physical or functional properties of the receptor-encoding gene product, for example, by binding of the receptor to neurotrophic factor or to an antibody which directly recognizes the receptor. Cells of the present invention may transiently or, preferably, constitutively and permanently express receptors or portions thereof.

In preferred embodiments, the present invention provides for cells that express receptors described herein or portions thereof and that also contain recombinant nucleic acid comprising an immediate early gene promoter [e.g. the fos or jun promoters (Gilman et al., 1986,Mol. Cell. Biol. 6: 4305–4316)]. When such a cell is exposed to a ligand that binds to the receptor, the binding secondarily induces transcription off the immediate early promoter. Such a cell may be used to detect receptor/ligand binding by measuring the transcriptional activity of the immediate early gene promoter, for example, by nuclear run-off analysis, Northern blot analysis, or by measuring levels of a gene controlled by the promoter. The immediate early promoter may be used to control the expression of fos or jun or any detectable gene product, including, but not limited to, any of the known reporter genes, such as a gene that confers hygromycin resistance (Murphy and Efstratiadis, 1987, Proc. Natl. Acad. Sci. U.S.A. 84: 8277–8281) chloramphenicol acetyltransferase (CAT), neomycin phosphotransferase (neo), beta-galactosidase beta-glucuronidase, beta-galactosidase, etc. of detecting or measuring neurotrophin activity.

Furthermore, the cells used in the assay systems of the invention may or may not be cells of the nervous system. For example, in a specific, nonlimiting embodiment of the invention, growth-factor dependent fibroblasts may be used as the basis for a signal transducing assay system. A fibroblast cell line that is growth factor dependent in serum-free media (e.g. as described in Zham and Goldfarb, 1986, Mol. Cell. Biol. 6: 3541–3544) may be transfected with a receptor-encoding gene, for instance by using a $CaPO_4$ transfection protocol with 5 micrograms of DNA of CMV-promoter-based expression vector comprising the dmk gene and one microgram of hygromycin-resistance gene-containing expression vector. After about 48 hours, the cells may then be selected for hygromycin resistance to identify positive transfectants. The cells may then be cultured for about three weeks in the presence of hygromycin, and then resistant colonies may be pooled. These cells may then be plated on tissue culture plates coated with poly-D-lysine and human fibronectin, and allowed to grow in DMEM plus 10% bovine calf serum for about four hours to allow the cells to bind to the plates. The serum-containing media may then be aspirated and the cells may be washed about three times with PBS to remove any residual serum. The cells may then be taken up with either serum free defined media (a 3:1 mixture of DMEM and Hams F12, supplemented with 8 mM sodium bicarbonate, 15 mM HEPES, $4\times10^{-6}$M $MnCl_2$, 3 mM histidine, $10^{-5}$M ethanolamine, $10^{-7}$M sodium selenite, 5 mg transferrin per liter, 200 mg bovine serum albumin-linoleic acid complex per liter gentamicin, penicillin, and streptomycin, 20 mM L-glutamine). Cells produced in this manner, then incubated with a factor capable of binding to Dmk may, after about 5 days in culture (replacing media and growth factors every 48 hours), be expected to be growing and proliferating; cells treated with an unrelated ligand at 100 ng/ml or in serum free-medium should not, however, proliferate. Further insight into the physiological role of Dmk will come from the definition of its ligand. Because the kinase domain of the Dmk protein appears to be related to other receptor tyrosine kinases, it is likely that this protein is involved in signal transduction in cells in which it is expressed. Accordingly, Dmk-binding ligands screened using the receptor described herein can be used to induce signal transduction in naturally occurring Dmk-expressing cells, which include cells found in the muscle tissue, as well in the heart, spleen, ovaries and retina as well as cells engineered to express the Dmk protein. It is contemplated that such ligands may promote the growth or survival of such cells. As described above, the present invention relates to a tyrosine kinase receptor that appears to be expressed in denervated muscle. According to the present invention, probes capable of recognizing these receptors may be used to identify diseases or disorders by measuring altered levels of the receptor in cells and tissues. Such diseases or disorders may, in turn, be treatable using ligands which bind these receptors. Such disorders include but are not limited to those in which atrophic or dystrophic change of muscle is the fundamental pathological finding. For example, muscle atrophy can result from denervation (loss of contact by the muscle with its nerve) due to nerve trauma; degenerative, metabolic or inflammatory neuropathy (e.g. Guillian-Barre syndrome), peripheral neuropathy, or damage to nerves caused by environmental toxins or drugs. In another embodiment, the muscle atrophy results from denervation due to a motor neuronopathy. Such motor neuronopathies include, but are not limited to: adult motor neuron disease, including Amyotrophic Lateral Sclerosis (ALS or Lou Gehrig's disease); infantile and juvenile spinal muscular atrophies, and autoimmune motor neuropathy with multifocal conduction block. In another embodiment, the muscle atrophy results from chronic disuse. Such disuse atrophy may stem from conditions including, but not limited to: paralysis due to stroke, spinal cord injury; skeletal immobilization due to trauma (such as fracture, sprain or dislocation) or prolonged bed rest. In yet another embodiment, the muscle atrophy results from metabolic stress or nutritional insufficiency, including, but not limited to, the cachexia of cancer and other chronic illnesses, fasting or rhabdomyolysis, endocrine disorders such as, but not limited to, disorders of the thyroid gland and diabetes. The muscle atrophy can also be due to a muscular dystrophy syndrome, including but not limited to the Duchenne, Becker, myotonic, Fascioscapulohumeral, Emery-Dreifuss, oculopharyngeal, scapulohumeral, limb girdle, and congenital types, and the dystrophy known as Hereditary Distal Myopathy. In a further embodiment, the muscle atrophy is due to a congenital myopathy, including, but not limited to Benign Congenital Hypotonia, Central Core disease, Nemaline Myopathy, and Myotubular (centronuclear) myopathy. In addition, Dmk and its associated ligand may be of use in the treatment of acquired (toxic or inflammatory) myopathies. Myopathies which occur as a consequence of an inflammatory disease of muscle, include, but not limited to polymyositis and dermatomyositis. Toxic myopathies may be due to agents, including, but are not limited to adiodarone, chloroquine, clofibrate, colchicine, doxorubicin, ethanol, hydroxychloroquine, organophosphates, perihexiline, and vincristine. Although not wishing to be bound by theory, preliminary mapping of the Dmk in mouse has revealed that the gene is localized to mouse chromosome 4 in a region of homology with human chromosome 9q. Mutations in mice that are associated with this region of chromosome 4 include the "wi" mutation (whirler), which results in symptoms of the shaker syndrome, including deafness, head-tossing, circling and hyperactivity (Lane, P. W., 963, J. Hered. 54: 263–266). Another mutation in mice that is associated with this region of chromosome 4 is the "vc" mutation (vacillans) which is associated with the symptoms of violent tremor when walking and with swaying of the hindquarters (Sirlin, J. L., 1956, J. Gienet. 54: 42–48).

In humans, the disease known as idiopathic torsion dystonia (ITD) is associated with a gene that has been mapped, through linkage analysis to human chromosome 9q band 34. This disease is characterized by sustained, involuntary muscle contractions, frequently causing twisting and repetitive movements or abnormal postures.

Should a defect in dmk be found to be associated with these diseases, the present invention may prove useful in gene therapy for the replacement of such gene in situ. Alternatively, probes utilizing a unique segment of the dmk gene may prove useful as a diagnostic for such disorders. The present invention provides for a method of diagnosing a neurological or other disorder in a patient comprising comparing the levels of expression of Dmk in a patient sample with the levels of expression of Dmk in a comparable sample from a healthy person, in which a difference in the levels of expression of Dmk in the patient compared to the healthy person indicates that a disorder in the patient may be primarily or secondarily related to Dmk metabolism. A patient sample may be any cell, tissue, or body fluid but is preferably muscle tissue or cerebral spinal fluid.

One variety of probe which may be used is anti-Dmk antibody or fragments thereof containing the binding domain of the antibody.

According to the invention, Dmk protein, or fragments or derivatives thereof, may be used as an immunogen to generate anti-Dmk antibodies. By providing for the production of relatively abundant amounts of Dmk protein using recombinant techniques for protein synthesis (based upon the Dmk nucleic acid sequences of the invention), the problem of limited quantities of Dmk has been obviated.

To further improve the likelihood of producing an anti-Dmk immune response, the amino acid sequence of Dmk may be analyzed in order to identify portions of the molecule which may be associated with increased immunogenicity. For example, the amino acid sequence may be subjected to computer analysis to identify surface epitopes which present computer-generated plots of hydrophilicity, surface probability, flexibility, antigenic index, amphiphilic helix, amphiphilic sheet, and secondary structure of Dmk. Alternatively, the deduced amino acid sequences of Dmk from different species could be compared, and relatively non-homologous regions identified; these non-homologous regions would be more likely to be immunogenic across various species.

For preparation of monoclonal antibodies directed toward Dmk, any technique which provides for the production of antibody molecules by continuous cell lines in culture may be used. For example, the hybridoma technique originally developed by Kohler and Milstein (1975, Nature 256: 495–497), as well as the trioma technique, the human B-cell hybridoma technique (Kozbor et al., 1983, Immunology Today 4: 72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies for therapeutic use may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80: 7308–7312; Kozbor et al., 1983, Immunology Today 4: 72–79; Olsson et al., 1982, Meth. Enzymol. 92: 3–16). Chimeric antibody molecules may be prepared containing a mouse antigen-binding domain with human constant regions (Morrison et al., 1984, Proc. Natl. Acad. Sci. U.S.A. 81: 6851, Takeda et al., 1985, Nature 314: 452).

Various procedures known in the art may be used for the production of polyclonal antibodies to epitopes of Dmk. For the production of antibody, various host animals can be immunized by injection with Dmk protein, or a fragment or derivative thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BOG (Bacille Calmette-Guerin) and *Corynebacterium parvum*.

A molecular clone of an antibody to a Dmk epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. The above mentioned probes may be used experimentally to identify cells or tissues which hitherto had not been shown to express Dmk. Furthermore, these methods may be used to identify the expression of Dmk by aberrant tissues, such as malignancies. In additional embodiments, these methods may be used diagnostically to compare the expression of Dmk in cells, fluids, or tissue from a patient suffering from a disorder with comparable cells, fluid, or tissue from a healthy person. Fluid is construed to refer to any body fluid, but particularly blood or cerebrospinal fluid. A difference in the levels of expression of Dmk in the patient compared to a healthy person may indicate that the patient's disorder may be primarily or secondarily related to Dmk metabolism. An increase in levels of Dmk, for example, could either indicate that the patient's disorder is associated with an increased sensitivity to normal levels of Dmk-binding ligand or, alternatively, may suggest that the patient's Dmk-binding ligand levels are low such that the number of receptors is increased by way of compensation. The present invention further provides for the use of soluble receptor (the extracellular domain) to counter the effect of ligand on Dmk expressing cells. Such blocking would be desirable, for example, if the cognate were found to have undesirable mitogenic properties.

EXAMPLE: CLONING OF THE cDNA ENCODING Dmk

MATERIALS AND METHODS

Tyrosine kinase homology domains were identified based on the alignments by Hanks et al. (1988) Science 241, 42–52. Highly conserved regions Asp-Leu-Ala-Ala-Arg-Asn (SEQ ID NO: 7) AND Asp-Val-Trp-Ser-Tyr-Gly (SEQ ID NO: 13) were used in designing the following degenerate oligonucleotide primers:

5'-TCTTGACTCGAGAYYTNGCNGCNMGNAA-3' (SEQ ID NO: 8)

5'-GAATTCGAGCTCCCRTANSWCCANACRTC-3' (SEQ ID NO: 15)

with which to prime PCR reactions using denervated muscle cDNAs. Resulting amplified DNA fragments were cloned by insertion into plasmids, sequenced and the DNA sequences were compared with those of all known tyrosine kinases. cDNA templates were generated by reverse transcription of denervated muscle tissue RNAs using oligo d(T) primers. PCR reactions were done at primer annealing temperatures of 40° C. Aliquots of the PCR reactions were subjected to electrophoresis on an agarose gel.

Size-selected amplified DNA fragments from these PCR reactions were cloned into plasmids as follows: Each PCR reaction was reamplified as described above, digested with XhoI and SacI to cleave sites in the termini of the primers (see below). XhoI/SacI-cut DNAs were purified by Magic PCR kit (from Promega) and cloned into compatible XhoI/SacI sites in the Bluescript II SK(+) plasmid, introduced into DH10B E. coli by electroporation, followed by plating of transformants on selective agar. Ampicillin-resistant bacterial colonies from PCR transformation were inoculated into 96-well microtiter plates and used for PCR using vector primers (T3 and T7) flanking the tyrosine kinase insert and these PCR fragments were analyzed by sequencing.

One of the cloned fragment sequences contained a segment of a novel tyrosine kinase domain, which was designated as Dmk. The sequence of the PCR-derived fragment corresponding to Dmk was used to generate PCR primers to obtain longer Dmk specific fragments by the RACE procedure. These longer Dmk probes were used as a hybridization probe to obtain full length Dmk cDNA clones from a rat denervated skeletal muscle cDNA library. DNA was sequenced by using the ABI 373A DNA sequencer and Taq Dyedeoxy Terminator Cycle Sequencing Kit (Applied Biosystems, Inc., Foster City, Calif.). The sequence of Dmk (FIG. 1; SEQ ID NO: 1) has a high degree of homology to members of the trk family of proteins. It was also found to be similar to the Jennings, et al. Torpedo RTK found in muscle.

RESULTS AND DISCUSSION

Oligonucleotide primers corresponding to conserved regions of known tyrosine kinase molecules were used to amplify and clone DNA sequences encoding novel orphan tyrosine kinase receptor molecules. The amino acid sequences of representatives from branches of the tyrosine kinase family and regions of homology within the catalytic domain of these proteins were used to design degenerate oligonucleotide primers. These primers were then used to prime PCR reactions using as template a rat denervated muscle cDNA library. Resulting amplified DNA fragments were then cloned into Bluescript II SK(+) plasmid, sequenced, and the DNA sequences compared with those of known tyrosine kinases. The sequence of a PCR fragment encoding a novel tyrosine kinase named Dmk was used to obtain more adjoining DNA sequence. A DNA fragment containing Dmk sequences was used as a probe to obtain a cDNA clone from a denervated skeletal muscle library. This clone encodes a novel tyrosine kinase receptor with a high degree of homology to members of the trk family of proteins. It was also found to be homologous to the Jennings, et al. Torpedo RTK.

FIG. 1 presents the nucleotide sequence (SEQ ID NO: 2) of the dmk clone.

EXAMPLE: IDENTIFICATION OF ADDITIONAL TYROSINE KINASES

The novel Dmk sequence is used to obtain homology segments among receptor tyrosine kinases which can now be used in combination with other homology segments. For example, an alignment of the Torpedo trk-related kinase with Dmk shows the following conserved protein segment:

Asp-Val-Trp-Ala-Tyr-Gly (SEQ ID NO: 3)

This homology "box" is not present in any other mammalian tyrosine kinase receptor. Degenerated oligonucleotides essentially based on this "box" in combination with either previously known or novel tyrosine kinase homology segments can be used to identify new tyrosine kinase receptors.

MATERIALS AND METHODS

The highly conserved regions between Dmk and Torpedo TRK Asp-Val-Trp-Ala-Tyr-Gly (SEQ ID NO: 3) as well as additional primers based on known regions of homology, such as SEQ ID NOS. 5, 7, 9 OR 11, are used in designing degenerate oligonucleotide primers with which to prime PCR reactions using cDNAs. cDNA templates are generated by reverse transcription of tissue RNAs using oligo d(T) or other appropriate primers. Aliquots of the PCR reactions are subjected to electrophoresis on an agarose gel. Resulting amplified DNA fragments are cloned by insertion into plasmids, sequenced and the DNA sequences are compared with those of all known tyrosine kinases.

Size-selected amplified DNA fragments from these PCR reactions are cloned into plasmids as follows. Each PCR reaction is reamplified as described above in Example 1, digested with XhoI and SacI to cleave sites in the termini of the primers (see below). XhoI/SacI-cut DNAs are cloned into compatible XhoI/SacI sites in a plasmid, introduced into E. coli by electroporation, followed by plating of transformants on selective agar. Ampicillin-resistant bacterial colonies from PCR transformation are inoculated into 96-well microtiter plates and individual colonies from these PCR clones are analyzed by sequencing of plasmid DNAs that are purified by standard plasmid miniprep procedures.

Cloned fragments containing a segment of a novel tyrosine kinase domain are used as hybridization probes to obtain full length cDNA clones from a cDNA library.

EXAMPLE: TISSUE SPECIFIC EXPRESSION OF Dmk

MATERIALS AND METHODS

A 680 nts fragment, containing the tyrosine kinase domain of Dmk, was radiolabeled and utilized in Northern analysis of various rat tissue specific RNAs. The rat tissue specific RNAs were fractionated by electrophoresis through a 1% agarose-formaldehyde gel followed by capillary transfer to a nylon membrane with 10× SSC. The RNAs were cross-linked to the membranes by exposure to ultraviolet light and hybridized at 65° C. to the radiolabeled Dmk probe in the presence of 0.5M NaPO4 (pH 7), 1% bovine serum albumin (Fraction V, Sigma), 7% SDS, 1 mM EDTA and 100 ng/ml sonicated, denatured salmon sperm DNA. The filter was washed at 65° C. with 2× SSC, 0.1% SDS and subjected to autoradiography for 5 days with one intensifying screen and X-ray film at −70° C. Ethidium bromide staining of the gel demonstrated that equivalent levels of total RNA were being assayed for the different samples.

RESULTS

Figure 3:
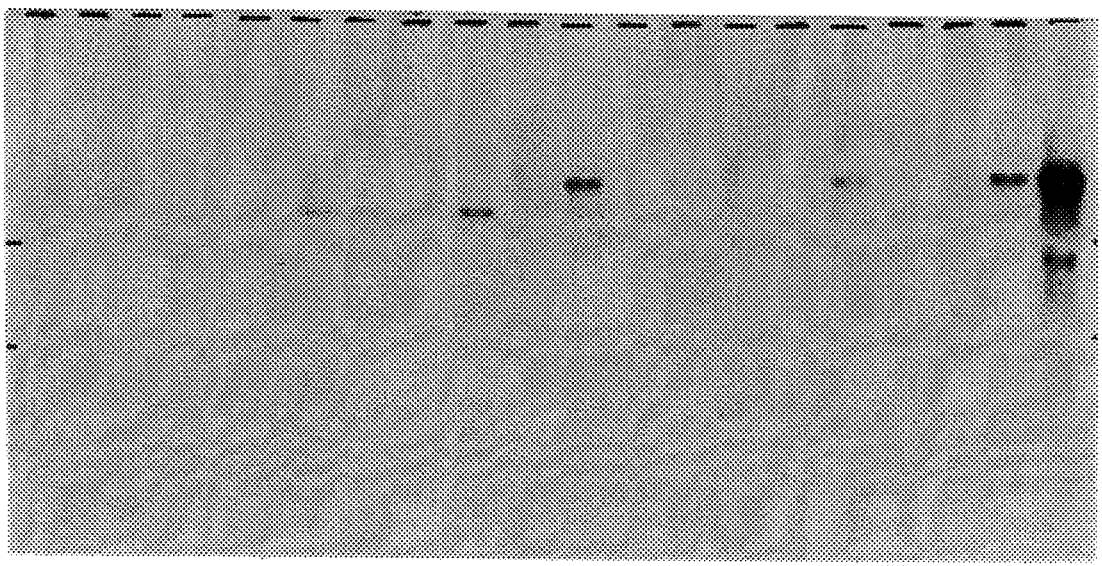
FIG. 3—Northern blot showing distribution of dmk in adult rat tissues. Lane 1: Brain; Lane 2: Olfactory bulb; Lane 3: Cortex; Lane 4: Hippocampus; Lane 5: Thalamus/hypothalamus; Lane 6: Midbrain; Lane 7: Hindbrain; Lane 8: Cerebellum; Lane 9: Spinal Cord; Lane 10: Thymus; Lane 11: Spleen; Lane 12: Liver; Lane 13: Kidney; Lane 14: Lung; Lane 15: Sciatic Nerve; Lane 16: Retina; Lane 17: Heart; Lane 18: Ovary; Lane 19: Muscle; Lane 20: Denervated muscle.

The Dmk probe hybridized strongly in adult rat tissue (FIG. 3) to a 7 kb transcript from denervated skeletal muscle, and weakly to normal muscle, retina, ovary, heart and spleen. Weaker levels of expression could also be found in liver, kidney and lung. It also hybridizes weakly to a shorter Dmk transcript of about 6 kb in brain, spinal cord and cerebellum. In embryonic tissue (FIG. 2), Dmk transcripts can be found in body, spinal cord, placenta and head at E12 and E 13. The high expression of Dmk in muscle and neural tissue suggests that the present invention, or the ligand associated with Dmk, may be utilized to treat disorders of the nervous system, specifically the wide array of neurological disorders affecting motor neurons (see discussion, supra) and the neuromuscular junction. Additionally, high expression of Dmk in heart tissue suggests that the present invention or the ligand associated with Dmk may be utilized to treat heart disease, and may, for example, have prophylactic use in preventing muscle loss during or following a cardiac event. (see discussion, supra). Expression of Dmk in retinal tissue suggests that the present invention may be utilized to treat retina related disorders, including but not limited to retinitis pigmentosa. Expression of Dmk in ovaries suggests that Dmk or the ligand associated with Dmk may be useful in the treatment of diseases or disorders involving the ovaries. Finally, expression of Dmk in spleen suggests that Dmk or the ligand associated with Dmk may be useful in the treatment of diseases or disorders involving the spleen.

EXAMPLE—CLONING AND EXPRESSION OF DMK RECEPTORBODY FOR AFFINITY-BASED STUDY OF DMK LIGAND INTERACTIONS

An expression construct was created that would yield a secreted protein consisting of the entire extracellular portion of the rat DMK receptor fused to the human immunoglobulin gamma-1 constant region (IgG1 Fc). This fusion protein is called a DMK "receptorbody" (RB), and would be normally expected to exist as a dimer in solution based on formation of disulfide linkages between individual IgG1 Fc tails. The Fc portion of the DMK RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding DMK receptor and from the human IgG1 Fc plasmid were ligated on either side of a short PCR-derived fragment that was designed so as to fuse, in-frame, the DMK and human IgG1 Fc protein-coding sequences. Thus, the resulting DMK ectodomain-Fc fusion protein precisely substituted the IgG1 Fc in place of the region spanning the DMK transmembrane and cytoplasmic domains. An alternative method of preparing RBs is described in Goodwin, et. al. Cell 73: 447–456 (1993).

Milligram quantities of DMK RB were obtained by cloning the DMK RB DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1-4 may be used. DNA encoding the DMK RB was cloned as an Eco RI-NotI fragment into the baculovirus transfer plasmid pVL1393. Plasmid DNA purified by cesium chloride density gradient centrifugation was recombined into viral DNA by mixing 3 mg of plasmid DNA with 0.5 mg of Baculo-Gold DNA (Pharminigen), followed by introduction into liposomes using 30 mg Lipofectin (GIBCO-BRL). DNA-liposome mixtures were added to SF-21AE cells ($2 \times 10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, Baculovirus Expression Vectors—A Laboratory Manual. 1992, New York: W.H. Freeman) except that the agarose overlay contained 125 mg/mL X-gal (5-bromo-4-chloro-3-indolyl-b-D-galactopyranoside; GIBCO-BRL). After 5 days of incubation at 27° C., non-recombinant plaques were scored by positive chromagenic reaction to the X-gal substrate, and their positions marked. Recombinant plaques were then visualized by addition of a second overlay containing 100 mg/mL MTT (3-[4,5-dimethylthiazol-2-yl] 2,5, diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vDMK receptorbody) were produced.

SF-21AE cells were cultured in serum free medium (SF-900 II, Gibco BRL) containing 1× antibiotic/antimycotic solution (Gibco BRL) and 25 mg/L Gentamycin (Gibco BRL). Pluronic F-68 was added as a surfactant to a final concentration of 1 g/L. Cultures (4L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase ($\sim 2 \times 10^6$ cells per mL), concentrated by centrifugation, and infected with 5 plaque forming units of vDMK receptorbody per cell. Cells and inoculum were brought to 400 mL with fresh medium, and virus was adsorbed for 2 hours at 27° C. in a spinner flask. The culture was then resuspended in a final volume of 8L with fresh serum-free medium, and the cells incubated in the bioreactor using the previously described conditions.

Culture medium from vDMK ReceptorBody-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 mm, Millipore)

and loaded on a protein A column (protein A sepharose 4 fast flow or HiTrap protein A, both from Pharmacia). The column was washed with PBS containing 0.5M NaCl until the absorbance at 280 nm decreased to baseline. The column was washed in PBS and eluted with 0.5M acetic acid. Column fractions were immediately neutralized by eluting into tubes containing 1M Tris pH 9. The peak fractions containing the DMK RB were pooled and dialyzed versus PBS.

EXAMPLE—SEQUENCING OF HUMAN Dmk RECEPTOR

In order to obtain the full coding sequence of the human Dmk receptor, oligonucleotides based on the rat sequence were utilized as PCR primers to amplify cDNA from a human muscle biopsy. The PCR fragment so produced was then sequenced and the resulting new sequence corresponded to a partial sequence of the human Dmk receptor. The novel partial human Dmk receptor sequence was then used to obtain further sequence through successive rounds of the RACE procedure. (Frohman, M. A. (1990), RACE: Rapid amplification of cDNA ends. in PCR Protocols, Innis, M. A. Gelfand, D. H., Snincky, J. J., and White, T. J. eds. Academic Press. San Diego).

This process was complemented by obtaining human genomic clones of Dmk and using the coding sequence of the genomic Dmk to design oligonucleotide primers used to amplify the biopsy cDNA. Stretches of the human Dmk cDNA sequence which were difficult to sequence, absent or presenting some ambiguity were confirmed, corrected or added from the human genomic Dmk sequence. Dmk cDNA variants produced by alternative splicing of Dmk transcripts may be obtained by using this sequence to obtain Dmk cDNA from human sources. The deduced amino acid sequence of the human Dmk receptor and the nucleotide sequence encoding it is set forth in FIG. 4 (SEQ ID NOS: 16 and 17). One of skill in the art will readily recognize that this sequence may be used to clone full length, naturally occurring cDNA sequences encoding the human Dmk receptor, which may vary slightly from the sequence set forth in FIG. 4 (SEQ ID NO: 17).

DEPOSIT OF MICROORGANISMS

A clone designated pBluescript SK-containing dmk was deposited with the American Type Culture Collection, 12301 Parklawn Drive, Rockville, Md. 20852 on Jul. 13, 1993 under ATCC Accession No. 75498.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

---

What is claimed is:

1. Isolated human Dmk receptor encoded by a nucleic acid molecule comprising a nucleotide sequence selected from the group consisting of:
   (a) a nucleotide sequence comprising the sequence encoding human Dmk receptor as set forth in SEQ. ID. NO. 17; and
   (b) a nucleotide sequence that, as a result of the degeneracy of the genetic code, differs from the nucleotide sequence of (a) and encodes human Dmk receptor.

2. A receptorbody comprising the extracellular domain of the human Dmk receptor of claim 1, fused to an immunoglobulin constant region.

3. The receptorbody of claim 2, wherein the constant region is the human immunoglobulin gamma-1 constant region.

4. An isolated Dmk receptor comprising an amino acid sequence as set forth in SEQ. ID. NO. 16.

5. A receptorbody comprising the extracellular domain of the human Dmk receptor of claim 4, fused to an immunoglobulin constant region.

6. The receptorbody of claim 5, wherein the constant region is the human immunoglobulin gamma-1 constant region.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 868 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO:1:

| Met | Arg | Glu | Leu | Val | Asn | Ile | Pro | Leu | Leu | Gln | Met | Leu | Thr | Leu | Val |
|---|---|---|---|---|---|---|---|---|---|---|---|---|---|---|---|
| 1 | | | | 5 | | | | | 10 | | | | | 15 | |
| Ala | Phe | Ser | Gly | Thr | Glu | Lys | Leu | Pro | Lys | Ala | Pro | Val | Ile | Thr | Thr |
| | | | 20 | | | | | 25 | | | | | 30 | | |
| Pro | Leu | Glu | Thr | Val | Asp | Ala | Leu | Val | Glu | Glu | Val | Ala | Thr | Phe | Met |
| | | 35 | | | | | 40 | | | | | 45 | | | |
| Cys | Ala | Val | Glu | Ser | Tyr | Pro | Gln | Pro | Glu | Ile | Ser | Trp | Thr | Arg | Asn |
| | 50 | | | | | 55 | | | | | 60 | | | | |
| Lys | Ile | Leu | Ile | Lys | Leu | Phe | Asp | Thr | Arg | Tyr | Ser | Ile | Arg | Glu | Asn |
| 65 | | | | | 70 | | | | | 75 | | | | | 80 |
| Gly | Gln | Leu | Leu | Thr | Ile | Leu | Ser | Val | Glu | Asp | Ser | Asp | Asp | Gly | Ile |
| | | | | 85 | | | | | 90 | | | | | 95 | |
| Tyr | Cys | Cys | Thr | Ala | Asn | Asn | Gly | Val | Gly | Gly | Ala | Val | Glu | Ser | Cys |
| | | | 100 | | | | | 105 | | | | | 110 | | |
| Gly | Ala | Leu | Gln | Val | Lys | Met | Lys | Pro | Lys | Ile | Thr | Arg | Pro | Pro | Ile |
| | | | 115 | | | | 120 | | | | | 125 | | | |

```
Asn Val Lys Ile Ile Glu Gly Leu Lys Ala Val Leu Pro Cys Thr Thr
    130             135                 140

Met Gly Asn Pro Lys Pro Ser Val Ser Trp Ile Lys Gly Asp Ser Ala
145             150                 155                 160

Leu Arg Glu Asn Ser Arg Ile Ala Val Leu Glu Ser Gly Ser Leu Arg
                165                 170                 175

Ile His Asn Val Gln Lys Glu Asp Ala Gly Gln Tyr Arg Cys Val Ala
            180                 185                 190

Lys Asn Ser Leu Gly Thr Ala Tyr Ser Lys Leu Val Lys Leu Glu Val
        195                 200                 205

Glu Val Phe Ala Arg Ile Leu Arg Ala Pro Glu Ser His Asn Val Thr
    210                 215                 220

Phe Gly Ser Phe Val Thr Leu Arg Cys Thr Ala Ile Gly Met Pro Val
225                 230                 235                 240

Pro Thr Ile Ser Trp Ile Glu Asn Gly Asn Ala Val Ser Ser Gly Ser
                245                 250                 255

Ile Gln Glu Asn Val Lys Asp Arg Val Ile Asp Ser Arg Leu Gln Leu
            260                 265                 270

Phe Ile Thr Lys Pro Gly Leu Tyr Thr Cys Ile Ala Thr Asn Lys His
        275                 280                 285

Gly Glu Lys Phe Ser Thr Ala Lys Ala Ala Ala Thr Val Ser Ile Ala
    290                 295                 300

Glu Trp Ser Lys Ser Gln Lys Glu Ser Lys Gly Tyr Cys Ala Gln Tyr
305                 310                 315                 320

Arg Gly Glu Val Cys Asp Ala Val Leu Val Lys Asp Ser Leu Val Phe
                325                 330                 335

Phe Asn Thr Ser Tyr Pro Asp Pro Glu Glu Ala Gln Glu Leu Leu Ile
            340                 345                 350

His Thr Ala Trp Asn Glu Leu Lys Ala Val Ser Pro Leu Cys Arg Pro
        355                 360                 365

Ala Ala Glu Ala Leu Leu Cys Asn His Leu Phe Gln Glu Cys Ser Pro
    370                 375                 380

Gly Val Leu Pro Thr Pro Met Pro Ile Cys Arg Glu Tyr Cys Leu Ala
385                 390                 395                 400

Val Lys Glu Leu Phe Cys Ala Lys Glu Trp Leu Ala Met Glu Gly Lys
                405                 410                 415

Thr His Arg Gly Leu Tyr Arg Ser Gly Met His Phe Leu Pro Val Pro
            420                 425                 430

Glu Cys Ser Lys Leu Pro Ser Met His Gln Asp Pro Thr Ala Cys Thr
        435                 440                 445

Arg Leu Pro Tyr Leu Asp Tyr Lys Lys Glu Asn Ile Thr Thr Phe Pro
    450                 455                 460

Ser Ile Thr Ser Ser Lys Pro Ser Val Asp Ile Pro Asn Leu Pro Ala
465                 470                 475                 480

Ser Thr Ser Ser Phe Ala Val Ser Pro Ala Tyr Ser Met Thr Val Ile
                485                 490                 495

Ile Ser Ile Met Ser Cys Phe Ala Val Phe Ala Leu Leu Thr Ile Thr
            500                 505                 510

Thr Leu Tyr Cys Cys Arg Arg Arg Arg Glu Trp Lys Asn Lys Lys Arg
        515                 520                 525

Glu Ser Ala Ala Val Thr Leu Thr Thr Leu Pro Ser Glu Leu Leu Leu
    530                 535                 540

Asp Arg Leu His Pro Asn Pro Met Tyr Gln Arg Met Pro Leu Leu Leu
545                 550                 555                 560
```

| | | | | | | | | | | | | | | |
|---|---|---|---|---|---|---|---|---|---|---|---|---|---|---|
| Asn | Pro | Lys | Leu | Leu | Ser | Leu | Glu | Tyr | Pro | Arg | Asn | Asn | Ile | Glu | Tyr |
| | | | | 565 | | | | | 570 | | | | | 575 |
| Val | Arg | Asp | Ile | Gly | Glu | Gly | Ala | Phe | Gly | Arg | Val | Phe | Gln | Ala | Arg |
| | | | 580 | | | | | 585 | | | | | 590 | | |
| Ala | Pro | Gly | Leu | Leu | Pro | Tyr | Glu | Pro | Phe | Thr | Met | Val | Ala | Val | Lys |
| | | | 595 | | | | | 600 | | | | | 605 | | |
| Met | Leu | Lys | Glu | Glu | Ala | Ser | Ala | Asp | Met | Gln | Ala | Asp | Phe | Gln | Arg |
| | | 610 | | | | 615 | | | | | 620 | | | | |
| Glu | Ala | Ala | Leu | Met | Ala | Glu | Phe | Asp | Asn | Pro | Asn | Ile | Val | Lys | Leu |
| 625 | | | | | 630 | | | | | 635 | | | | | 640 |
| Leu | Gly | Val | Cys | Ala | Val | Gly | Lys | Pro | Met | Cys | Leu | Leu | Phe | Glu | Tyr |
| | | | | 645 | | | | | 650 | | | | | 655 | |
| Met | Ala | Tyr | Gly | Asp | Leu | Asn | Glu | Phe | Leu | Arg | Ser | Met | Ser | Pro | His |
| | | | 660 | | | | | 665 | | | | | 670 | | |
| Thr | Val | Cys | Ser | Leu | Ser | His | Ser | Asp | Leu | Ser | Thr | Arg | Ala | Arg | Val |
| | | | 675 | | | | | 680 | | | | | 685 | | |
| Ser | Ser | Pro | Gly | Pro | Pro | Pro | Leu | Ser | Cys | Ala | Glu | Gln | Leu | Cys | Ile |
| | | 690 | | | | 695 | | | | | 700 | | | | |
| Ala | Arg | Gln | Val | Ala | Ala | Gly | Met | Ala | Tyr | Leu | Ser | Glu | Arg | Lys | Phe |
| 705 | | | | | 710 | | | | | 715 | | | | | 720 |
| Val | His | Arg | Asp | Leu | Ala | Thr | Arg | Asn | Cys | Leu | Val | Gly | Glu | Asn | Met |
| | | | | 725 | | | | | 730 | | | | | 735 | |
| Val | Val | Lys | Ile | Ala | Asp | Phe | Gly | Leu | Ser | Arg | Asn | Ile | Tyr | Ser | Ala |
| | | | 740 | | | | | 745 | | | | | 750 | | |
| Asp | Tyr | Tyr | Lys | Ala | Asp | Gly | Asn | Asp | Ala | Ile | Pro | Ile | Arg | Trp | Met |
| | | 755 | | | | | 760 | | | | | 765 | | | |
| Pro | Pro | Glu | Ser | Ile | Phe | Tyr | Asn | Arg | Tyr | Thr | Thr | Glu | Ser | Asp | Val |
| | 770 | | | | | 775 | | | | | 780 | | | | |
| Trp | Ala | Tyr | Gly | Val | Val | Leu | Trp | Glu | Ile | Phe | Ser | Tyr | Gly | Leu | Gln |
| 785 | | | | | 790 | | | | | 795 | | | | | 800 |
| Pro | Tyr | Tyr | Gly | Met | Ala | His | Glu | Glu | Val | Ile | Tyr | Tyr | Val | Arg | Asp |
| | | | | 805 | | | | | 810 | | | | | 815 | |
| Gly | Asn | Ile | Leu | Ala | Cys | Pro | Glu | Asn | Cys | Pro | Leu | Glu | Leu | Tyr | Asn |
| | | | 820 | | | | | 825 | | | | | 830 | | |
| Leu | Met | Arg | Leu | Cys | Trp | Ser | Lys | Leu | Pro | Ala | Asp | Arg | Pro | Ser | Phe |
| | | 835 | | | | | 840 | | | | | 845 | | | |
| Cys | Ser | Ile | His | Arg | Ile | Leu | Gln | Arg | Met | Cys | Glu | Arg | Ala | Glu | Gly |
| | 850 | | | | | 855 | | | | | 860 | | | | |
| Thr | Val | Gly | Val | | | | | | | | | | | | |
| 865 | | | | | | | | | | | | | | | |

( 2 ) INFORMATION FOR SEQ ID NO:2:

( i ) SEQUENCE CHARACTERISTICS:
        ( A ) LENGTH: 2869 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

```
GAATTCGGCA CGAGCAAACA GTCATTAGTG GACGACTCTA TTGTAATAAA CTGTGCTTTA        60

AAATGTAAAC CAGGGAGCGT TTTTTTTCCT CACATTGTCC AGAAGCAACC TTTCTTCCTG       120

AGCCTGGATT AATCATGAGA GAGCTCGTCA ACATTCCACT GTTACAGATG CTCACCCTGG       180
```

| | | | | | |
|---|---|---|---|---|---|
| TTGCCTTCAG | CGGGACCGAG | AAACTTCCAA | AAGCCCCTGT | CATCACCACG | CCTCTTGAAA | 240
| CTGTAGATGC | CTTAGTTGAA | GAAGTGGCGA | CTTTCATGTG | CGCCGTGGAA | TCCTACCCTC | 300
| AGCCTGAAAT | TTCTTGGACC | AGAAATAAAA | TTCTCATCAA | GCTGTTTGAC | ACCCGCTACA | 360
| GCATCCGAGA | GAACGGTCAG | CTCCTCACCA | TCCTGAGTGT | GGAGGACAGT | GATGATGGCA | 420
| TCTACTGCTG | CACAGCCAAC | AATGGAGTGG | GAGGAGCGGT | GGAAAGTTGT | GGCGCCCTGC | 480
| AAGTGAAGAT | GAAGCCTAAA | ATAACTCGTC | CTCCATCAA | TGTAAAAATA | ATTGAGGGAT | 540
| TGAAAGCAGT | CCTACCGTGC | ACTACGATGG | GTAACCCCAA | GCCATCCGTG | TCCTGGATTA | 600
| AGGGGACAG | TGCTCTCAGG | GAAAATTCCA | GGATTGCAGT | TCTTGAATCT | GGGAGTTTAA | 660
| GGATCCATAA | TGTGCAAAAG | GAAGACGCAG | GACAGTACCG | ATGTGTGGCA | AAAACAGCC | 720
| TGGGCACAGC | TTACTCCAAA | CTGGTGAAGC | TGGAAGTGGA | GGTTTTGCA | AGAATCCTGC | 780
| GTGCTCCTGA | ATCCACAAT | GTCACCTTTG | GTTCCTTTGT | AACCCTACGC | TGCACAGCAA | 840
| TAGGCATGCC | TGTCCCCACC | ATCAGCTGGA | TTGAAAACGG | AAATGCTGTT | TCTTCAGGTT | 900
| CCATTCAAGA | GAATGTGAAA | GACCGAGTGA | TTGACTCAAG | ACTCCAGCTC | TTTATCACAA | 960
| AGCCAGGACT | CTACACATGC | ATAGCTACCA | ATAAGCATGG | AGAGAAATTC | AGTACCGCAA | 1020
| AGGCTGCAGC | CACTGTCAGT | ATAGCAGAAT | GGAGCAAATC | ACAGAAAGAA | AGCAAAGGCT | 1080
| ACTGTGCCCA | GTACAGAGGG | GAGGTGTGTG | ATGCCGTCCT | GGTGAAAGAC | TCTCTTGTCT | 1140
| TCTTCAACAC | CTCCTATCCC | GACCCTGAGG | AGGCCCAAGA | GCTGCTGATC | CACACTGCGT | 1200
| GGAATGAACT | CAAGGCTGTG | AGCCCACTCT | GCCGACCAGC | TGCCGAGGCT | CTGCTGTGTA | 1260
| ATCACCTCTT | CCAGGAGTGC | AGCCCTGGAG | TGCTACCTAC | TCCTATGCCC | ATTTGCAGAG | 1320
| AGTACTGCTT | GGCAGTAAAG | GAGCTCTTCT | GTGCAAAGGA | ATGGCTGGCA | ATGGAAGGGA | 1380
| AGACCCACCG | CGGACTCTAC | AGATCCGGGA | TGCATTTCCT | CCCGGTCCCG | GAGTGCAGCA | 1440
| AGCTTCCCAG | CATGCACCAG | GACCCCACAG | CCTGCACAAG | ACTGCCGTAT | TTAGATTATA | 1500
| AAAAGAAAA | CATAACAACA | TTCCCGTCCA | TAACGTCCTC | CAAGCCGAGC | GTGGACATTC | 1560
| CAAACCTGCC | TGCCTCCACG | TCTTCCTTCG | CCGTCTCGCC | TGCGTACTCC | ATGACTGTCA | 1620
| TCATCTCCAT | CATGTCCTGC | TTTGCGGTGT | TGCTCTCCT | CACCATCACT | ACTCTCTATT | 1680
| GCTGCCGAAG | GAGGAGAGAG | TGGAAAAATA | AGAAAAGAGA | GTCGGCAGCG | GTGACCCTCA | 1740
| CCACATTGCC | TTCCGAGCTC | CTGCTGGACA | GGCTGCATCC | CAACCCCATG | TACCAGAGGA | 1800
| TGCCACTCCT | TCTGAATCCC | AAGTTGCTCA | GCCTGGAGTA | TCCGAGGAAT | AACATCGAGT | 1860
| ATGTCAGAGA | CATCGGAGAG | GGAGCGTTTG | GAAGGGTCTT | TCAAGCGAGG | GCCCCAGGCT | 1920
| TGCTTCCTTA | TGAACCCTTC | ACTATGGTGG | CTGTGAAGAT | GCTGAAGGAG | GAGGCCTCCG | 1980
| CAGATATGCA | GGCAGACTTT | CAGAGGGAGG | CAGCCCTCAT | GGCGGAGTTT | GACAACCCCA | 2040
| ACATTGTGAA | GCTCTTAGGT | GTGTGTGCTG | TTGGGAAGCC | AATGTGCCTG | CTCTTTGAAT | 2100
| ATATGGCCTA | TGGTGACCTC | AATGAGTTCC | TCCGAAGCAT | GTCCCCTCAC | ACTGTGTGCA | 2160
| GCCTCAGCCA | CAGTGACCTG | TCCACGAGGG | CTCGGGTGTC | CAGCCCTGGT | CCTCCACCCC | 2220
| TGTCTTGTGC | GGAACAGCTC | TGTATTGCCA | GGCAAGTGGC | AGCTGGCATG | GCCTACCTGT | 2280
| CGGAGCGCAA | GTTTGTCCAT | CGGGACTTAG | CTACCAGGAA | CTGCCTGGTT | GGAGAGAACA | 2340
| TGGTGGTGAA | AATTGCAGAC | TTTGGCCTCT | CTAGGAACAT | CTACTCCGCA | GACTACTACA | 2400
| AAGCTGATGG | AAACGATGCT | ATACCTATCC | GCTGGATGCC | ACCCGAGTCT | ATCTTCTACA | 2460
| ACCGCTACAC | CACGGAGTCA | GATGTGTGGG | CTTATGGCGT | GGTCCTCTGG | GAGATCTTCT | 2520
| CCTATGGACT | GCAGCCCTAC | TATGGAATGG | CCCATGAGGA | GGTCATTTAC | TATGTGAGAG | 2580

| | | | | | |
|---|---|---|---|---|---|
| ATGGTAACAT | CCTTGCCTGC | CCTGAGAACT | GTCCCTTGGA | ACTGTACAAC | CTTATGCGCC | 2640
| TATGTTGGAG | CAAGCTGCCT | GCAGACAGAC | CCAGCTTCTG | CAGTATCCAC | CGGATCCTGC | 2700
| AGCGCATGTG | CGAGAGAGCA | GAGGGAACGG | TAGGCGTCTA | AGGTTGACCA | TGCTCAAACA | 2760
| ACACCCAGGA | GGATCTTTTC | AGACTGCGAG | CTGGAGGGAT | CCTAAAGCAG | AGGGCGNATA | 2820
| AGNNCAGATA | GGAAGAGTTT | ATCTCAGGCA | GCACGTNCAG | TTGGTTGTT | | 2869

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:3:

Asp Val Trp Ala Tyr Gly
1               5

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GAATTCGAGC TCCCRWANGC CCANACRTC        29

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:5:

Asp Leu Ala Thr Arg Asn
1               5

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TCTTGACTCG AGA Y Y TNGCN ACNMGNAA        28

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:7:

Asp Leu Ala Ala Arg Asn
1               5

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

TCTTGACTCG AGA Y Y TNGCN GCNMGNAA                                28

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:9:

Asp Val Trp Ser Leu Gly
1               5

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

GAATTCGAGC TCCCRTANSW CCANACRTC                                 29

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:11:

Asp Val Trp Ser Phe Gly
1               5

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

GAATTCGAGC TCCCRAANSW CCANACRTC 29

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: unknown ( i i ) MOLECULE TYPE: peptide ( x i ) SEQUENCE DESCRIPTION: SEQ ID NO:13:

```
Asp  Val  Trp  Ser  Tyr  Gly
 1                    5
```

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

GAATTCGAGC TCCCNARNSW CCANACRTC 29

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

GAATTCGAGC TCCCRTANSW CCANACRTC 29

( 2 ) INFORMATION FOR SEQ ID NO:16:

( i ) SEQUENCE CHARACTERISTICS:
        ( A ) LENGTH: 869 amino acids
        ( B ) TYPE: amino acid
        ( C ) STRANDEDNESS:
        ( D ) TOPOLOGY: unknown ( i i ) MOLECULE TYPE: protein ( x i ) SEQUENCE DESCRIPTION: SEQ ID NO:16:

```
Met  Arg  Glu  Leu  Val  Asn  Ile  Pro  Leu  Val  His  Ile  Leu  Thr  Leu  Val
 1                    5                         10                        15

Ala  Phe  Ser  Gly  Thr  Glu  Lys  Leu  Pro  Lys  Ala  Pro  Val  Ile  Thr  Thr
               20                         25                        30

Pro  Leu  Glu  Thr  Val  Asp  Ala  Leu  Val  Glu  Glu  Val  Ala  Thr  Phe  Met
               35                         40                        45

Cys  Ala  Val  Glu  Ser  Tyr  Pro  Gln  Pro  Glu  Ile  Ser  Trp  Thr  Arg  Asn
               50                         55                        60

Lys  Ile  Leu  Ile  Lys  Leu  Phe  Asp  Thr  Arg  Tyr  Ser  Ile  Arg  Glu  Asn
 65                         70                        75                     80

Gly  Gln  Leu  Leu  Thr  Ile  Leu  Ser  Val  Glu  Asp  Ser  Asp  Asp  Gly  Ile
```

-continued

```
                        85                          90                          95
    Tyr  Cys  Cys  Thr  Ala  Asn  Asn  Gly  Val  Gly  Gly  Ala  Val  Glu  Ser  Cys
                   100                      105                      110

Gly  Ala  Leu  Gln  Val  Lys  Met  Lys  Pro  Lys  Ile  Thr  Arg  Pro  Pro  Ile
                   115                      120                      125

Asn  Val  Lys  Ile  Ile  Glu  Gly  Leu  Lys  Ala  Val  Leu  Pro  Cys  Thr  Thr
         130                      135                      140

Met  Gly  Asn  Pro  Lys  Pro  Ser  Val  Ser  Trp  Ile  Lys  Gly  Asp  Ser  Pro
    145                      150                      155                      160

Leu  Arg  Glu  Asn  Ser  Arg  Ile  Ala  Val  Leu  Glu  Ser  Gly  Ser  Leu  Arg
                        165                      170                      175

Ile  His  Asn  Val  Gln  Lys  Glu  Asp  Ala  Gly  Gln  Tyr  Arg  Cys  Val  Ala
                   180                      185                      190

Lys  Asn  Ser  Leu  Gly  Thr  Ala  Tyr  Ser  Lys  Val  Val  Lys  Leu  Glu  Val
                   195                      200                      205

Glu  Val  Phe  Ala  Arg  Ile  Leu  Arg  Ala  Pro  Glu  Ser  His  Asn  Val  Thr
         210                      215                      220

Phe  Gly  Ser  Phe  Val  Thr  Leu  His  Cys  Thr  Ala  Thr  Gly  Ile  Pro  Val
    225                      230                      235                      240

Pro  Thr  Ile  Thr  Trp  Ile  Glu  Asn  Gly  Asn  Ala  Val  Ser  Ser  Gly  Ser
                        245                      250                      255

Ile  Gln  Glu  Ser  Val  Lys  Asp  Arg  Val  Ile  Asp  Ser  Arg  Leu  Gln  Leu
                   260                      265                      270

Phe  Ile  Thr  Lys  Pro  Gly  Leu  Tyr  Thr  Cys  Ile  Ala  Thr  Asn  Lys  His
                   275                      280                      285

Gly  Glu  Lys  Phe  Ser  Thr  Ala  Lys  Ala  Ala  Ala  Thr  Ile  Ser  Ile  Ala
         290                      295                      300

Glu  Trp  Ser  Lys  Pro  Gln  Lys  Asp  Asn  Lys  Gly  Tyr  Cys  Ala  Gln  Tyr
    305                      310                      315                      320

Arg  Gly  Glu  Val  Cys  Asn  Ala  Val  Leu  Ala  Lys  Asp  Ala  Leu  Val  Phe
                        325                      330                      335

Leu  Asn  Thr  Ser  Tyr  Ala  Asp  Pro  Glu  Glu  Ala  Gln  Glu  Leu  Leu  Val
                   340                      345                      350

His  Thr  Ala  Trp  Asn  Glu  Leu  Lys  Val  Val  Ser  Pro  Val  Cys  Arg  Pro
                   355                      360                      365

Ala  Ala  Glu  Ala  Leu  Leu  Cys  Asn  His  Ile  Phe  Gln  Glu  Cys  Ser  Pro
         370                      375                      380

Gly  Val  Val  Pro  Thr  Pro  Ile  Pro  Ile  Cys  Arg  Glu  Tyr  Cys  Leu  Ala
    385                      390                      395                      400

Val  Lys  Glu  Leu  Phe  Cys  Ala  Lys  Glu  Trp  Leu  Val  Met  Glu  Glu  Lys
                        405                      410                      415

Thr  His  Arg  Gly  Leu  Tyr  Arg  Ser  Glu  Met  His  Leu  Leu  Ser  Val  Pro
                   420                      425                      430

Glu  Cys  Ser  Lys  Leu  Pro  Ser  Met  His  Trp  Asp  Pro  Thr  Ala  Cys  Ala
                   435                      440                      445

Arg  Leu  Pro  His  Leu  Asp  Tyr  Asn  Lys  Glu  Asn  Leu  Lys  Thr  Phe  Pro
         450                      455                      460

Pro  Met  Thr  Ser  Ser  Lys  Pro  Ser  Val  Asp  Ile  Pro  Asn  Leu  Pro  Ser
    465                      470                      475                      480

Ser  Ser  Ser  Ser  Ser  Phe  Ser  Val  Ser  Pro  Thr  Tyr  Ser  Met  Thr  Val
                        485                      490                      495

Ile  Ile  Ser  Ile  Met  Ser  Ser  Phe  Ala  Ile  Phe  Val  Leu  Leu  Thr  Ile
                   500                      505                      510
```

```
Thr  Thr  Leu  Tyr  Cys  Cys  Arg  Arg  Lys  Gln  Trp  Lys  Asn  Lys  Lys
     515                520                525

Arg  Glu  Ser  Ala  Ala  Val  Thr  Leu  Thr  Thr  Leu  Pro  Ser  Glu  Leu  Leu
     530                535                540

Leu  Asp  Arg  Leu  His  Pro  Asn  Pro  Met  Tyr  Gln  Arg  Met  Pro  Leu  Leu
545                550                555                               560

Leu  Asn  Pro  Lys  Leu  Leu  Ser  Leu  Glu  Tyr  Pro  Arg  Asn  Asn  Ile  Glu
               565                570                               575

Tyr  Val  Arg  Asp  Ile  Gly  Glu  Gly  Ala  Phe  Gly  Arg  Val  Phe  Gln  Ala
               580                585                590

Arg  Ala  Pro  Gly  Leu  Leu  Pro  Tyr  Glu  Pro  Phe  Thr  Met  Val  Ala  Val
          595                600                     605

Lys  Met  Leu  Lys  Glu  Glu  Ala  Ser  Ala  Asp  Met  Gln  Ala  Asp  Phe  Gln
     610                615                620

Arg  Glu  Ala  Ala  Leu  Met  Ala  Glu  Phe  Asp  Asn  Pro  Asn  Ile  Val  Lys
625                630                635                               640

Leu  Leu  Gly  Val  Cys  Ala  Val  Gly  Lys  Pro  Met  Cys  Leu  Leu  Phe  Glu
               645                650                               655

Tyr  Met  Ala  Tyr  Gly  Asp  Leu  Asn  Glu  Phe  Leu  Arg  Ser  Met  Ser  Pro
               660                665                     670

His  Thr  Val  Cys  Ser  Leu  Ser  His  Ser  Asp  Leu  Ser  Met  Arg  Ala  Gln
               675                680                     685

Val  Ser  Ser  Pro  Gly  Pro  Pro  Pro  Leu  Ser  Cys  Ala  Glu  Gln  Leu  Cys
     690                695                     700

Ile  Ala  Arg  Gln  Val  Ala  Ala  Gly  Met  Ala  Tyr  Leu  Ser  Glu  Arg  Lys
705                710                715                               720

Phe  Val  His  Arg  Asp  Leu  Ala  Thr  Arg  Asn  Cys  Leu  Val  Gly  Glu  Asn
               725                730                               735

Met  Val  Val  Lys  Ile  Ala  Asp  Phe  Gly  Leu  Ser  Arg  Asn  Ile  Tyr  Ser
               740                745                     750

Ala  Asp  Tyr  Tyr  Lys  Ala  Asn  Glu  Asn  Asp  Ala  Ile  Pro  Ile  Arg  Trp
          755                760                     765

Met  Pro  Pro  Glu  Ser  Ile  Phe  Tyr  Asn  Arg  Tyr  Thr  Thr  Glu  Ser  Asp
     770                775                     780

Val  Trp  Ala  Tyr  Gly  Val  Val  Leu  Trp  Glu  Ile  Phe  Ser  Tyr  Gly  Leu
785                790                795                               800

Gln  Pro  Tyr  Tyr  Gly  Met  Ala  His  Glu  Glu  Val  Ile  Tyr  Tyr  Val  Arg
               805                810                815

Asp  Gly  Asn  Ile  Leu  Ser  Cys  Pro  Glu  Asn  Cys  Pro  Val  Glu  Leu  Tyr
               820                825                     830

Asn  Leu  Met  Arg  Leu  Cys  Trp  Ser  Lys  Leu  Pro  Ala  Asp  Arg  Pro  Ser
          835                840                     845

Phe  Thr  Ser  Ile  His  Arg  Ile  Leu  Glu  Arg  Met  Cys  Glu  Arg  Ala  Glu
     850                855                860

Gly  Thr  Val  Ser  Val
865
```

( 2 ) INFORMATION FOR SEQ ID NO:17:

( i ) SEQUENCE CHARACTERISTICS:
        ( A ) LENGTH: 2610 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:17:

| | | | | | |
|---|---|---|---|---|---|
| ATGAGAGAGC | TCGTCAACAT | TCCACTGGTA | CATATTCTTA | CTCTGGTTGC | CTTCAGCGGA | 60
| ACTGAGAAAC | TTCCAAAAGC | TCCTGTCATC | ACCACTCCTC | TTGAAACAGT | GGATGCCTTA | 120
| GTTGAAGAAG | TGGCTACTTT | CATGTGTGCA | GTGGAATCCT | ACCCCAGCC | TGAGATTTCC | 180
| TGGACTAGAA | ATAAAATTCT | CATTAAACTC | TTTGACACCC | GGTACAGCAT | CCGGGAGAAT | 240
| GGGCAGCTCC | TCACCATCCT | GAGTGTGGAA | GACAGTGATG | ATGGCATTTA | CTGCTGCACG | 300
| GCCAACAATG | GTGTGGGAGG | AGCTGTGGAG | AGTTGTGGAG | CCCTGCAAGT | GAAGATGAAA | 360
| CCTAAAATAA | CTCGCCCTCC | CATAAATGTG | AAATAATAG | AGGGATTAAA | AGCAGTCCTA | 420
| CCATGTACTA | CAATGGGTAA | TCCCAAACCA | TCAGTGTCTT | GGATAAAGGG | AGACAGCCCT | 480
| CTCAGGGAAA | ATTCCCGAAT | TGCAGTTCTT | GAATCTGGGA | GCTTGAGGAT | TCATAACGTA | 540
| CAAAAGGAAG | ATGCAGGACA | GTATCGATGT | GTGGCAAAAA | ACAGCCTCGG | ACAGCATAT | 600
| TCCAAAGTGG | TGAAGCTGGA | AGTTGAGGTT | TTGCCAGGA | TCCTGCGGGC | TCCTGAATCC | 660
| CACAATGTCA | CCTTTGGCTC | CTTTGTGACC | CTGCACTGTA | CAGCAACAGG | CATTCCTGTC | 720
| CCCACCATCA | CCTGGATTGA | AAACGGAAAT | GCTGTTTCTT | CTGGGTCCAT | TCAAGAGAGT | 780
| GTGAAAGACC | GAGTGATTGA | CTCAAGACTG | CAGCTGTTTA | TCACCAAGCC | AGGACTCTAC | 840
| ACATGCATAG | CTACCAATAA | GCATGGGGAG | AAGTTCAGTA | CTGCCAAGGC | TGCAGCCACC | 900
| ATCAGCATAG | CAGAATGGAG | TAAACCACAG | AAAGATAACA | AAGGCTACTG | CGCCCAGTAC | 960
| AGAGGGGAGG | TGTGTAATGC | AGTCCTGGCA | AAAGATGCTC | TTGTTTTCT | CAACACCTCC | 1020
| TATGCGGACC | CTGAGGAGGC | CCAAGAGCTA | CTGGTCCACA | CGGCCTGGAA | TGAACTGAAA | 1080
| GTAGTGAGCC | CAGTCTGCCG | GCCAGCTGCT | GAGGCTTTGT | TGTGTAACCA | CATCTTCCAG | 1140
| GAGTGCAGTC | CTGGAGTAGT | GCCTACTCCT | ATTCCCATTT | GCAGAGAGTA | CTGCTTGGCA | 1200
| GTAAAGGAGC | TCTTCTGCGC | AAAAGAATGG | CTGGTAATGG | AAGAGAAGAC | CCACAGAGGA | 1260
| CTCTACAGAT | CCGAGATGCA | TTTGCTGTCC | GTGCCAGAAT | GCAGCAAGCT | TCCAGCATG | 1320
| CATTGGGACC | CCACGGCCTG | TGCCAGACTG | CCACATCTAG | ATTATAACAA | AGAAAACCTA | 1380
| AAAACATTCC | CACCAATGAC | GTCCTCAAAG | CCAAGTGTGG | ACATTCCAAA | TCTGCCTTCC | 1440
| TCCTCCTCTT | CTTCCTTCTC | TGTCTCACCT | ACATACTCCA | TGACTGTAAT | AATCTCCATC | 1500
| ATGTCCAGCT | TTGCAATATT | TGTGCTTCTT | ACCATAACTA | CTCTCTATTG | CTGCCGAAGA | 1560
| AGAAAACAAT | GGAAAATAA | GAAAGAGAA | TCAGCAGCAG | TAACCCTCAC | CACACTGCCT | 1620
| TCTGAGCTCT | TACTAGATAG | ACTTCATCCC | AACCCCATGT | ACCAGAGGAT | GCCGCTCCTT | 1680
| CTGAACCCCA | AATTGCTCAG | CCTGGAGTAT | CCAAGGAATA | ACATTGAATA | TGTGAGAGAC | 1740
| ATCGGAGAGG | GAGCGTTTGG | AAGGGTGTTT | CAAGCAAGGG | CACCAGGCTT | ACTTCCCTAT | 1800
| GAACCTTTCA | CTATGGTGGC | AGTAAAGATG | CTCAAAGAAG | AAGCCTCGGC | AGATATGCAA | 1860
| GCGGACTTTC | AGAGGGAGGC | AGCCCTCATG | GCAGAATTTG | ACAACCCTAA | CATTGTGAAG | 1920
| CTATTAGGAG | TGTGTGCTGT | CGGGAAGCCA | ATGTGCCTGC | TCTTTGAATA | CATGGCCTAT | 1980
| GGTGACCTCA | ATGAGTTCCT | CCGCAGCATG | TCCCCTCACA | CCGTGTGCAG | CCTCAGTCAC | 2040
| AGTGACTTGT | CTATGAGGGC | TCAGGTCTCC | AGCCCTGGGC | CCCCACCCCT | CTCCTGTGCT | 2100
| GAGCAGCTTT | GCATTGCCAG | GCAGGTGGCA | GCTGGCATGG | CTTACCTCTC | AGAACGTAAG | 2160
| TTTGTTCACC | GAGATTTAGC | CACCAGGAAC | TGCCTGGTGG | GCGAGAACAT | GGTGGTGAAA | 2220
| ATTGCCGACT | TTGGCCTCTC | CAGGAACATC | TACTCAGCAG | ACTACTACAA | AGCTAATGAA | 2280
| AACGACGCTA | TCCCTATCCG | TTGGATGCCA | CCAGAGTCCA | TTTTTTATAA | CCGCTACACT | 2340

| | | | | | |
|---|---|---|---|---|---|
| ACAGAGTCTG | ATGTGTGGGC | CTATGGCGTG | GTCCTCTGGG | AGATCTTCTC | CTATGGCCTG | 2400 |
| CAGCCCTACT | ATGGGATGGC | CCATGAGGAG | GTCATTTACT | ACGTGCGAGA | TGGCAACATC | 2460 |
| CTCTCCTGCC | CTGAGAACTG | CCCCGTGGAG | CTGTACAATC | TCATGCGTCT | ATGTTGGAGC | 2520 |
| AAGCTGCCTG | CAGACAGACC | CAGTTTCACC | AGTATTCACC | GAATTCTGGA | ACGCATGTGT | 2580 |
| GAGAGGGCAG | AGGGAACTGT | GAGTGTCTAA | | | | 2610 |